US006984403B2

(12) United States Patent
Hagen et al.

(10) Patent No.: US 6,984,403 B2
(45) Date of Patent: Jan. 10, 2006

(54) AZITHROMYCIN DOSAGE FORMS WITH REDUCED SIDE EFFECTS

(75) Inventors: Timothy A. Hagen, East Lyme, CT (US); Julian B. Lo, Old Lyme, CT (US); Avinash G. Thombre, East Lyme, CT (US); Scott M. Herbig, East Lyme, CT (US); Leah Elizabeth Appel, Bend, OR (US); Marshall David Crew, Bend, OR (US); Dwayne Thomas Friesen, Bend, OR (US); David Keith Lyon, Bend, OR (US); Scott Baldwin McCray, Bend, OR (US); James Blair West, Bend, OR (US)

(73) Assignee: Pfizer Inc., New York, NY (US)

( * ) Notice: Subject to any disclaimer, the term of this patent is extended or adjusted under 35 U.S.C. 154(b) by 22 days.

(21) Appl. No.: 10/763,340

(22) Filed: Jan. 23, 2004

(65) Prior Publication Data

US 2005/0123627 A1    Jun. 9, 2005

Related U.S. Application Data

(60) Provisional application No. 60/527,084, filed on Dec. 4, 2003.

(51) Int. Cl.
    *A61K 9/14*    (2006.01)

(52) U.S. Cl. ............... 424/489; 424/400; 424/464; 424/451

(58) Field of Classification Search .......... 424/490, 424/489, 464, 484, 465, 400, 451
See application file for complete search history.

(56) References Cited

U.S. PATENT DOCUMENTS

| 2,955,956 | A | 10/1960 | Baugh et al. ............... 117/100 |
| 4,053,264 | A | 10/1977 | King ............................ 425/8 |
| 4,086,346 | A | 4/1978 | Bocker et al. ............. 424/253 |
| 4,092,089 | A | 5/1978 | Bocker et al. ............. 425/10 |
| 4,293,570 | A | 10/1981 | Vadasz ....................... 426/3 |
| 4,474,768 | A | 10/1984 | Bright ....................... 424/180 |
| 4,517,359 | A | 5/1985 | Kobrehel et al. ........... 536/7.4 |
| 4,675,140 | A | 6/1987 | Sparks et al. ............. 264/4.3 |
| 4,874,611 | A | 10/1989 | Wilson et al. ............ 424/410 |

(Continued)

FOREIGN PATENT DOCUMENTS

EP    0080341    6/1983

(Continued)

OTHER PUBLICATIONS

Foulds, G., et al., "The effects of an antacid or cimetidine on the serum concentrations of azithromycin", J. Clin. Pharmacol. 1991 Feb.; 31(2): 164-7 (Abstract).

(Continued)

*Primary Examiner*—Thurman K. Page
*Assistant Examiner*—Pili A. Hawes
(74) *Attorney, Agent, or Firm*—Gregg C. Benson; B. Timothy Creagan; Lance Y. Liu

(57) ABSTRACT

The present invention is related to an oral dosage form comprising an effective amount of an alkalizing agent and an azithromycin multiparticulate wherein said multiparticulate comprises azithromycin, a glyceride which comprises glyceryl monobehenate, glyceryl dibehenate, glyceryl tribehenate, or a mixture thereof and a poloxamer. Typically, the oral dosage form includes any suitable oral dosing means such as a powder for oral suspension, a unit dose packet or sachet, a tablet or a capsule.

48 Claims, 3 Drawing Sheets

U.S. PATENT DOCUMENTS

| | | | |
|---|---|---|---|
| 4,931,285 A | 6/1990 | Edgren et al. | 424/473 |
| 4,957,681 A | 9/1990 | Klimesch et al. | 264/211.23 |
| 4,963,531 A | 10/1990 | Remington et al. | 514/29 |
| 5,019,302 A | 5/1991 | Sparks et al. | 264/8 |
| 5,024,842 A | 6/1991 | Edgren et al. | 424/473 |
| 5,047,244 A | 9/1991 | Sanvordeker et al. | 424/435 |
| 5,064,650 A | 11/1991 | Lew | 424/435 |
| 5,084,287 A | 1/1992 | Ghebre-Sellassie et al. | 424/495 |
| 5,100,592 A | 3/1992 | Sparks et al. | 264/7 |
| 5,143,662 A | 9/1992 | Chesterfield et al. | 264/8 |
| 5,160,743 A | 11/1992 | Edgren et al. | 424/473 |
| 5,169,645 A | 12/1992 | Shukla et al. | 424/499 |
| 5,183,690 A | 2/1993 | Carr et al. | 427/213.31 |
| 5,194,262 A | 3/1993 | Goldberg et al. | 424/401 |
| 5,196,199 A | 3/1993 | Fuisz | 424/401 |
| 5,213,810 A | 5/1993 | Steber | 424/490 |
| 5,236,734 A | 8/1993 | Fuisz | 426/641 |
| 5,292,657 A | 3/1994 | Rutherford et al. | 435/243 |
| 5,348,758 A | 9/1994 | Fuisz et al. | 426/660 |
| 5,380,473 A | 1/1995 | Bogue et al. | 264/11 |
| 5,405,617 A | 4/1995 | Gowan, Jr. et al. | 424/464 |
| 5,407,676 A | 4/1995 | Fuisz | 424/401 |
| 5,429,836 A | 7/1995 | Fuisz | 426/601 |
| 5,433,951 A | 7/1995 | Serajuddin et al. | 424/486 |
| 5,456,932 A | 10/1995 | Fuisz et al. | 426/548 |
| 5,461,089 A | 10/1995 | Handyside et al. | 523/171 |
| 5,500,162 A | 3/1996 | Theisen et al. | 264/9 |
| 5,501,858 A | 3/1996 | Fuisz | 424/439 |
| 5,505,983 A | 4/1996 | Kamada | 424/2.21 |
| 5,518,730 A | 5/1996 | Fuisz | 424/426 |
| 5,539,000 A | 7/1996 | Leonard | 514/682 |
| 5,549,917 A | 8/1996 | Cherukuri et al. | 426/96 |
| 5,556,652 A | 9/1996 | Cherukuri et al. | 426/5 |
| 5,569,467 A | 10/1996 | Ruiz | 424/489 |
| 5,582,855 A | 12/1996 | Cherukuri | 426/5 |
| 5,597,416 A | 1/1997 | Fuisz et al. | 127/30 |
| 5,597,844 A | 1/1997 | Chauhan et al. | 514/400 |
| 5,601,761 A | 2/1997 | Hoffman et al. | 264/4.3 |
| 5,605,889 A | 2/1997 | Curatolo et al. | 514/29 |
| 5,633,006 A | 5/1997 | Catania et al. | 424/441 |
| 5,683,720 A | 11/1997 | Myers et al. | 424/489 |
| 5,690,959 A | 11/1997 | Palepu et al. | 424/472 |
| 5,705,190 A | 1/1998 | Broad et al. | 424/465 |
| 5,707,646 A | 1/1998 | Yajima et al. | 424/439 |
| 5,733,577 A | 3/1998 | Myers et al. | 424/488 |
| 5,741,519 A | 4/1998 | Rosenberg et al. | 424/464 |
| 5,744,180 A | 4/1998 | Cherukuri et al. | 426/99 |
| 5,747,058 A | 5/1998 | Tipton et al. | 424/423 |
| 5,766,521 A | 6/1998 | Le Thiesse et al. | 264/7 |
| 5,792,474 A | 8/1998 | Rauchfuss | 424/489 |
| 5,824,342 A | 10/1998 | Cherukuri et al. | 424/484 |
| 5,840,334 A | 11/1998 | Raiden et al. | 424/464 |
| 5,849,223 A | 12/1998 | Myers et al. | 264/15 |
| 5,851,553 A | 12/1998 | Myers et al. | 424/488 |
| 5,851,555 A | 12/1998 | Sanghvi et al. | 424/464 |
| 5,855,905 A | 1/1999 | Pinkus | 242/486 |
| 5,869,098 A | 2/1999 | Misra et al. | 424/484 |
| 5,869,101 A | 2/1999 | Moller et al. | 424/489 |
| 5,883,103 A | 3/1999 | Burnside et al. | 514/262 |
| 5,891,845 A | 4/1999 | Myers | 514/11 |
| 5,912,030 A | 6/1999 | Huznec et al. | 426/3 |
| 5,919,489 A | 7/1999 | Saleki-Gerhardt et al. | 424/501 |
| 5,935,600 A | 8/1999 | Cherukuri et al. | 424/489 |
| 5,948,407 A | 9/1999 | McGuinness et al. | 424/184.1 |
| 5,952,004 A | 9/1999 | Rudnic et al. | 424/455 |
| 5,958,452 A | 9/1999 | Oshlack et al. | 424/457 |
| 5,965,161 A | 10/1999 | Oshlack et al. | 424/457 |
| 5,965,164 A | 10/1999 | Fuisz et al. | 424/489 |
| 5,972,373 A | 10/1999 | Yajima et al. | 424/439 |
| 5,980,941 A | 11/1999 | Raiden et al. | 424/464 |
| 6,010,718 A | 1/2000 | Al-Razzak et al. | 424/464 |
| 6,013,280 A | 1/2000 | Frisbee et al. | 424/464 |
| 6,048,541 A | 4/2000 | Misra et al. | 424/401 |
| 6,051,253 A | 4/2000 | Zettler et al. | 424/465 |
| 6,068,859 A | 5/2000 | Curatolo et al. | 424/490 |
| 6,077,541 A | 6/2000 | Chen et al. | 424/480 |
| 6,083,430 A | 7/2000 | Fuisz et al. | 264/5 |
| 6,086,920 A | 7/2000 | Frisbee et al. | 424/489 |
| 6,090,830 A | 7/2000 | Myers et al. | 514/356 |
| 6,103,264 A | 8/2000 | Hoffmann et al. | 424/468 |
| 6,117,452 A | 9/2000 | Ahlgren et al. | 424/468 |
| 6,139,872 A | 10/2000 | Walsh | 424/464 |
| 6,165,512 A | 12/2000 | Mezaache et al. | 424/489 |
| 6,221,368 B1 | 4/2001 | Breitenbach et al. | 424/400 |
| 6,221,395 B1 * | 4/2001 | Maggi et al. | 424/475 |
| 6,245,903 B1 | 6/2001 | Karimian et al. | 536/7.4 |
| 6,248,363 B1 | 6/2001 | Patel et al. | 424/497 |
| 6,261,599 B1 | 7/2001 | Oshlack et al. | 424/457 |
| 6,268,489 B1 | 7/2001 | Allen et al. | 536/7.4 |
| 6,270,804 B1 | 8/2001 | Getz et al. | 424/490 |
| 6,328,993 B1 | 12/2001 | Linder et al. | 424/451 |
| 6,335,033 B2 | 1/2002 | Oshlack et al. | 424/457 |
| 6,365,574 B2 | 4/2002 | Singer et al. | 514/29 |
| 6,383,510 B1 | 5/2002 | Linder et al. | 424/436 |
| 6,395,300 B1 | 5/2002 | Straub et al. | 424/489 |
| 6,423,345 B2 | 7/2002 | Bernstein et al. | 424/501 |
| 6,479,540 B1 * | 11/2002 | Constantinides et al. | 514/458 |
| 6,500,459 B1 | 12/2002 | Chhabra et al. | 424/474 |
| 6,551,616 B1 | 4/2003 | Notario et al. | 424/464 |
| 6,569,463 B2 | 5/2003 | Patel et al. | 424/497 |
| 6,576,258 B1 | 6/2003 | Kofler et al. | 424/458 |
| 6,645,528 B1 | 11/2003 | Straub et al. | 424/489 |
| 6,682,759 B2 | 1/2004 | Lim et al. | 424/468 |
| 6,689,390 B2 | 2/2004 | Bernstein et al. | 424/501 |
| 6,692,767 B2 | 2/2004 | Burnside et al. | 424/489 |
| 6,706,283 B1 * | 3/2004 | Appel et al. | 424/473 |
| 2001/0003590 A1 | 6/2001 | Joshim et al. | |
| 2001/0006650 A1 | 7/2001 | Burnside | |
| 2002/0009433 A1 | 1/2002 | Curatolo et al. | |
| 2002/0025342 A1 | 2/2002 | Linder et al. | 424/489 |
| 2002/0044968 A1 | 4/2002 | Van Langerich | 424/469 |
| 2003/0165563 A1 | 9/2003 | Murphy et al. | 424/465 |
| 2003/0190365 A1 | 10/2003 | Fargione et al. | 424/489 |
| 2003/0228357 A1 | 12/2003 | Johnson et al. | 424/465 |
| 2004/0014951 A1 | 1/2004 | Dumic et al. | 536/7.1 |
| 2004/0023898 A1 | 2/2004 | Dunne | |
| 2004/0121003 A1 | 6/2004 | Chickering, III et al. | 424/465 |
| 2005/0026851 A1 | 2/2005 | Danilovski et al. | 514/28 |

FOREIGN PATENT DOCUMENTS

| | | |
|---|---|---|
| EP | 0109253 | 5/1984 |
| EP | 0582396 | 2/1994 |
| EP | 0925789 | 6/1999 |
| EP | 0943341 | 9/1999 |
| EP | 0776658 | 2/2000 |
| EP | 1127580 | 8/2001 |
| GB | 2066070 | 7/1981 |
| GB | 2091097 | 7/1982 |
| IN | 187487 | 5/2000 |
| WO | WO9107171 | 5/1991 |
| WO | WO9400112 | 1/1994 |
| WO | WO9427557 | 12/1994 |
| WO | WO9509601 | 4/1995 |
| WO | WO9806714 | 2/1998 |
| WO | WO9818610 | 5/1998 |
| WO | WO9846239 | 10/1998 |
| WO | WO9856357 | 12/1998 |
| WO | WO9903453 | 1/1999 |
| WO | WO9924031 | 5/1999 |
| WO | WO0026285 | 5/2000 |
| WO | WO0057886 | 10/2000 |
| WO | WO0142221 | 6/2001 |
| WO | WO0178688 | 10/2001 |

| WO | WO0185135 | 11/2001 |
| WO | WO0224174 | 3/2002 |
| WO | WO0318031 | 3/2003 |
| WO | WO3032922 | 4/2003 |
| WO | WO0337304 | 5/2003 |
| WO | WO0353402 | 7/2003 |
| WO | WO0383834 | 8/2003 |
| WO | WO3068191 | 8/2003 |
| WO | WO0400865 | 12/2003 |
| WO | WO3105810 | 12/2003 |
| WO | WO4009608 | 1/2004 |
| WO | WO4035063 | 4/2004 |
| WO | WO4087096 | 10/2004 |

OTHER PUBLICATIONS

Amsden, G.W., et al., "Serum and WBC pharmacokinetics of 1500 mg of azithromycin when given either as a single dose or over a 3 day period in healthy volunteers", J. Antimicrobial Chemotherapy (2001), 47(1), 61-66 (Abstract).

Barber, J., "Assignments of the $^{13}$C and $_1$H NMR Spectra of Azithromycin in CDCl$_3$," *Magnetic Resonance in Chemistry* 29:7(1991)740-743.

Barthelemy, P., et al., "Compritol® 888 ATO: An Innovative Hot-Melt Coating Agent for Prolonged-Release Drug Formulations," *Europ. J. Pharmaceut. and Biopharmaceutics*, 47(1999)87-90.

Bhagwatwar, H., et al., "Preparation of Drug-Containing Wax Microspheres Using a Melt Dispersion Technique," *Pharmaceutical Research*, 6:7(1989)S-177, Abstract No. PD 1201.

Breitenbach, J., et al., "Solid Dispersions by an Integrated Melt Extrusion System," *Proceed. Int'l Symp. Control Re. Bioact. Materials*, 25(1998)804-805.

Craig, D.Q.M., "The Physical Characterisation of Gelucire 50/13," *Bulletin Technique Gattefosse*, 89(1996)39-51.

DeMan, J.M., et al., "Thermal Analysis Microscopy for the Study of Phase Changes in Fats," *Food Microstructure*, 4(1985)233-239.

Eldem T., et al., "Polymorphic Behavior of Sprayed Lipid Micropellets and its Evaluation by Differential Scanning Calorimetry and Scanning Electron Microscopy," *Pharmaceutical Research*, 8:2(1991)178-184.

Eldern, T., et al., "Optimization of Spray-Dried and -Congealed Lipid Micropellets and Characterization of Their Surface Morphology by Scanning Electron Microscopy," Pharmaceutical Research, 8:1(1991)47-54.

Emas, M., and H. Nyqvist, "Methods of Studying Aging and Stabilization of Spray-Congealed Solid Dispersions with Carnauba Wax. 1. Microcalorimetric Investigation," *Int'l J. Pharmaceutics*, 197(2000)117-127.

Faham, A., et al., "Hot-Melt Coating Technology. I. Influence of Compritol 888 Ato and Granule Size on Theophyline Release," *Drug Dev. Industrial Pharm.*, 26:2(2000)167-176.

Follonier, N., et al, "Hot-Melt Extruded Pellets for the Sustained Release of Highly Dosed Freely Soluble Drugs," *Proceed. Intern. Symp. Control. Release Bioactive Materials*, 18(1991)578-579.

Forster, A., et al., "Characterization of Glass Solutions of Poorly Water-Soluble Drugs Produced by Melt Extrusion with Hydrophific Amorphous Polymers, " *J. Pharmacy Pharmacology*, 53(2001)303-315.

Foulds, G., et al., "The Absence of an Effect of Food on the Bioavailability of Azithromycin Administered as Tablets, Sachet or Suspension," *J. Antimicrobial Chemotherapy*, 37:Suppl. C(1996)37-44.

Gattefosse, "Gelucire®—Pharmaceutical Excipients for Oral Semi-Solid Formulations," Technical Dossier, 2$^{nd}$ edition, Gattefosse s.a., Cedex, France (1996).

Ghali, E.S., et al., "Thermal Treatment of Beads with Wax for Controlled Release," *Drug Development and Industrial Pharmacy*, 15:9(1989)1311-1328.

Hancock, B.C., and G. Zografi, "The Relationship Between the Glass Transition Temperature and the Water Content of Amorphous Pharmaceutical Solids," *Pharmaceutical Research*, 11:4(1994)471-477.

Joachim, J., et al., "Le Compritol", Etudes Galenique, Physique et Statstique, *APGI*, IV(1989)291-296.

Johnson, D.E., et al., "A New Method for Coating Glass Beads for Use in Gas Chromatography of Chloropromazine and its Metabolites," Source unknown, and date unknown. (may be 1964-1965).

Jorgensen, K., et al., "Dissolution Stability of Multiparticulate Controlled Release Tablets," *Int'l J. Pharmaceutics*, 153(1997)1-11.

Meshall, M.M., et al., "Optimization of Theophylline Release from Tablets Containing Compritol," *S.T.P. Pharma Sciences*, 5:6(1995)429-434.

Perez, M. deLos A, et al., "Sustained Release Phenylpropanolamine Hydrochloride from Compritol ATO-888 Matrix," *Pharmaceutical Research*, 9:10(1992)S-162, Abstract No. PT6191.

Perez, M.A., et al., "Sustained Release Phenylpropanolamine Hydrochloride from ATO 888 Matrix," PRHSJ, 12: 4(1993)263-267.

Perissutti, B., et al., "Solid Dispersions of Carbamazepine with Gelucire 44/14 and 50/13," *S.T.P. Pharma Sciences*, 10:6(2000)479-484.

Physician's Desk Reference, Information cited on ZITHROMAX® capsules (equivalent to 250 mg azithromycin), tablets (equivalent to 600 mg azithromycin), and oral suspension (equivalent to 1g azithromycin).

Reilly, W.J. Jr., and J.B. Schwartz, "A Potential Controlled Release Wax Matrix Excipient," *Pharmaceutical Research*, 8:10(1991)98, supplement, Abstract No. TP6108.

Reis, R. and F. Moll, "Matrix Formation of Polyglycolic Acid Tablets by Annealing," *European J. Pharm. and Biopharm.*, 40:1(1994)14-18.

Rxlist.com, "Azithromycin," description of drug, categories, brand names, from internet website, Mar. 14, 2001.

San Vincente, A., et al., "Effect of Aging on the Release of Salbutamol Sulfate from Lipid Matrices," *Int'l J. Pharmaceutics*, 208(2000)13-21).

Schwartz, J.B., et al., "A Potential Controlled Release Wax Matrix Excipient for Tablets," *Pharmaceutical Research*, 9:10(1992)S-162, Abstract No. PT6189.

Schwartz, J.B., et al., Preliminary Evaluation of Controlled Release Agents for Tablets, *Pharmaceutical Research*, 9:10 (1992)S-162, Abstract No. PT6190.

Sugao, H., et al, "Taste Masking of Bitter Drug Powder without Loss of Bioavailability by Heat Treatment of Wax-Coated Microparticles," *J. Pharmaceutical Sci.*, 87:1(1998) 96-100.

Thomasen, L.J., et al., "Prolonged Release Matrix Pellets Prepared by Melt Pelletization. I. Process Variables," *Drug Development and Industrial Pharmacy*, 19:15(1993)187-1887.

Wang, A.E. and J.B. Schwartz, "Effect of Temperature on Drug Release from Wax Matrix Tablets After Thermal Treatment," *Pharmaceutical Research*, 11:10(1994)S-155. Abstract No. 6099.

Zhang, Y.-E., et al., Effect of Processing Methods and Heat Treatment on the Formation of Wax Matrix Tablets for Sustained Drug Release, *Pharm. Dev. Technol.*, 6:2(2001) 131-144.

Arguendas, A., "Single Dose Therapy in Otitis Media, *Clinical Microbiology and Infection*," Abstract, S130, vol. 5, Supplemental 3, (1999).

Block, S., et al., "Single-Dose Azithromycin (30 mg/kg) in Acute Otitis Media," ICAAC, New Orleans, La, Sep. 7-10, 2003, Abstract 174.

Curatolo, W., et al., "Site-Specific Absorption and Toleration of Azithromycin," Proceedings Intern. Symposium Rel. Bioact. Mater., 23, 1996.

Luke, D.R., et al, "Clinical Pharmacology of Azithromycin Given at Various Sites Along the Gastrointestinal Tract in Healthy Subjects," pp. 464-468.

Physicians Desk Reference, "*Appendix A Summary of Pediatric Suspension Commercial Products*," 55th edition, Phase III Clinical Dosage Form Nomination, pp 19 and 28 (2001).

Pfizer, Inc., Zithromax [package insert], "*Zithromax (azithromycin tablets) and (azithromycin for oral suspension)*," www.pfizer.com/download/uspi _zithromax.pdf (2004).

* cited by examiner

AZITHROMYCIN DOSAGE FORMS WITH REDUCED SIDE EFFECTS

This application is a nonprovisional application of provisional application Ser. No. 60/527,084, filed Dec. 4, 2003.

BACKGROUND OF THE INVENTION

Azithromycin is an antibiotic which is administered orally or intravenously, to treat various infections, particularly infections of the urinary tract, bronchial tract, lungs, sinuses and the middle ear.

Oral dosing of azithromycin can result in adverse gastrointestinal (GI) side effects such as nausea, cramping, diarrhea and vomiting in a significant number of patients. Such GI side effects can also occur in non-human mammals, e.g., dogs. In combined clinical studies of azithromycin involving 3,995 human patients (all dose levels combined), 9.6% of patients reported GI side effects; the most frequent of these side effects were diarrhea (3.6%), nausea (2.6%), and abdominal pain (2.5%) Hopkins, 91 *Am. J. Med.* 40S (suppl 3A 1991).

The frequency of these adverse effects increase with higher dose levels of azithromycin. In treating adult humans, for a single 1 gram dose, administered in an oral suspension, the reported incidence of various GI side effects was 7% diarrhea/loose stools, 5% nausea, 5% abdominal pain, and 2% vomiting (U.S. Package Insert for Zithromax® azithromycin for oral suspension). However, for a single 2 gram, administered in an oral suspension, the reported incidence of various GI side effects was 14% diarrhea/loose stools, 7% abdominal pain, and 7% vomiting (Ibid.).

Similarly, in treating pediatric humans, by administering an oral suspension containing 10 mg/kg on Day 1 and 5 mg/kg on days 2–5, the reported incidence of various GI side effects was 4% diarrhea/loose stools, 2% abdominal pain, and 2% vomiting (Ibid.), while, for a single 30 mg/kg dose, administered in an oral suspension, the reported incidence of various GI side effects was 6.4% diarrhea/loose stools, 1.7% nausea, and 4% vomiting (Ibid.).

Antacids, which are alkalizing agents that are provided in large doses to raise stomach pH from about 1–3 to about 4–7, may provide a patient with relief from diarrhea, cramping, and gastric upset. However, patients have been cautioned against simultaneously taking an antacid, particularly those containing aluminum or magnesium, with azithromycin, as antacids have been shown to reduce azithromycin maximum serum concentration $C_{max}$ by 24% (Ibid.). Further, to avoid antacid caused interference with azithromycin absorption, patients have also been advised to separate the administration of azithromycin and antacid doses by at least two hours.

Presently, small amounts, about 132 mg or less, of the alkalizing agent anhydrous tribasic sodium phosphate are used in commercial dosage forms of azithromycin to mask the bitter taste of azithromycin by reducing the solubility of azithromycin before swallowing. Further, in treating uncomplicated gonococcal infections, two single dose packets of azithromycin, which each contain 88 mg of anhydrous tribasic sodium phosphate, are concurrently administered in a single dose to a patient in need thereof.

More recently, azithromycin controlled release dosage forms have been prepared, as described in U.S. Pat. No. 6,068,859, that reduce the gastrointestinal side effects, resulting from an administered dose of azithromycin, as compared to an equivalent dose of commercial immediate release azithromycin capsules. However, the bioavailability of many of the controlled release dosage forms, specifically exemplified therein, were subsequently found to be less than their immediate release equivalents.

Therefore, what is needed is an azithromycin dosage form that has a bioavailability similar to, and gastrointestinal side effects less than, an equivalent dose of immediate release azithromycin.

SUMMARY OF THE INVENTION

The present invention relates to an oral dosage form of azithromycin comprising azithromycin and an effective amount of an alkalizing agent. Preferably, said oral dosage form comprises an effective amount of an alkalizing agent and an azithromycin multiparticulate wherein said multiparticulate comprises azithromycin, a mixture of glyceryl mono-, di- and tribehenates, and a poloxamer.

The present invention further relates to an oral suspension comprising azithromycin, an effective amount of an alkalizing agent and a vehicle. Preferably, the azithromycin is in multiparticulate form. More preferably, the multiparticulates comprise azithromycin, a mixture of glyceryl mono-, di- and tribehenates, and a poloxamer.

Even more preferably, the azithromycin oral dosage form and oral suspension further comprise 300 mg to 400 mg of tribasic sodium phosphate, 200 mg to 300 mg of magnesium hydroxide, and multiparticulates, wherein said multiparticulates comprise (i) azithromycin, (ii) a mixture of glyceryl monobehenate, glyceryl dibehenate and glyceryl tribehenate, and (iii) poloxamer 407, and wherein said dosage form contains about 1.5 gA to about 4 gA of azithromycin.

In addition, the present invention also relates to a method for reducing gastrointestinal side effects, associated with administering azithromycin to a mammal, comprising contiguously administering azithromycin and an effective amount of alkalizing agent to said mammal wherein the frequency of gastrointestinal side effects is lower than that experienced by administering an equal dose of azithromycin without said alkalizing agent. In this method, it is preferable that the multiparticulates comprise (i) azithromycin, (ii) a mixture of glyceryl monobehenate, glyceryl dibehenate and glyceryl tribehenate, and (iii) a poloxamer.

The present invention further relates to a method of treating a bacterial or protozoal infection in a mammal in need thereof comprising contiguously administering to said mammal an oral dosage form wherein said oral dosage form comprises azithromycin and an effective amount of an alkalizing agent. Preferably, in this method, between 250 mgA and 7 gA of azithromycin are administered to a human. More preferably, 1.5 gA to 3 gA of azithromycin are administered to a human, even more preferably in a single dose. Also more preferably, for a pediatric human weighing 30 kg or less, between 45 mgA/kg and 75 mgA/kg of azithromycin are administered to said child, even more preferably in a single dose.

The present invention additionally relates to azithromycin multiparticulates comprising azithromycin, a surfactant; and a pharmaceutically acceptable carrier.

DETAILED DESCRIPTION OF THE INVENTION

Figure 1:
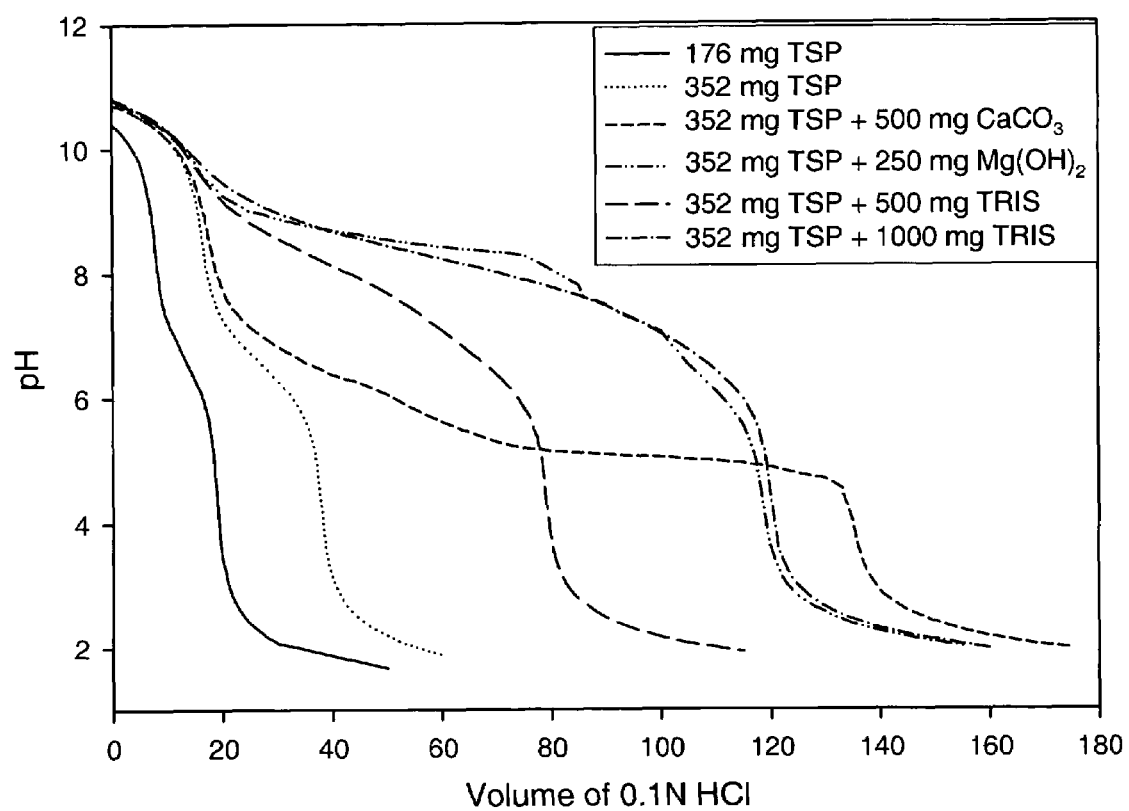
FIG. 1, which is further discussed in Example 1, shows the effects on pH of titrating different alkalizing agents with increasing volumes of 0.1N HCl.

As used in the present invention, the term "about" means the specified value ±10% of the specified value.

As used in the present invention, the terms "a" or "an" mean one or more. For example, the term "an alkalizing agent" means one or more alkalizing agents, the term "a carrier" means one or more carriers, and the term "a dissolution enhancer" means one or more dissolution enhancers.

The term "alkalizing agent", as used herein, means a pharmaceutically acceptable excipient which will raise the pH in a constituted suspension or in a patient's stomach after being orally administered to said patient.

The term "pharmaceutically acceptable", as used herein, means that which is compatible with other ingredients of the composition, and not deleterious to the recipient thereof.

The term "constituted suspension" means that the powder has been mixed with a vehicle and forms an "oral suspension". In this oral suspension, the azithromycin and excipients may be (a) completely suspended in the vehicle or (b) partially suspended in the vehicle and partially in solution in the vehicle. Oral suspensions of the present invention include vehicles containing azithromycin which is suspended within the vehicle, or wherein the azithromycin is temporarily suspended, in the vehicle after shaking, stirring or mixing.

A vehicle of the present invention comprises unflavored water, flavored water, or a natural or artificial fruit, or otherwise flavored, aqueous solution such as a beverage.

In the present invention, the alkalizing agent, excipients and vehicle are pharmaceutically acceptable.

An "effective amount of an alkalizing agent", as used herein, means an amount of one or more alkalizing agents which, when administered in combination with azithromycin, provides a relative degree of improvement in toleration in terms of the percentage of recipients tolerating azithromycin administration, without GI side effects, relative to a control dosage form containing the same amount of active azithromycin.

A "relative degree of improvement in toleration" is defined as the ratio of (1) the percentage adverse events arising from the administration of an immediate release control dosage form to (2) the percentage adverse events arising from the administration of a controlled release multiparticulate dosage form of the present invention, where the immediate release control dosage form and the controlled release multiparticulate dosage form contain the same amount of azithromycin. The immediate release control dosage form may be any conventional immediate release dosage form, such as Zithromax® tablets, capsules, or single-dose packets for oral suspension. For example, if an immediate release control dosage form provides a percentage adverse events arising from the administration of 20% while the multiparticulate dosage form of the present invention provides a percentage adverse events arising from the administration of 10%, then the relative degree of improvement in toleration is 20%÷10% or 2.

The term "oral dosage form" includes a plurality of devices that collectively deliver, by oral ingestion, the desired amount of azithromycin, to achieve a desired dose of azithromycin. Typically, the oral dosage form is a powder for oral suspension, a unit dose packet or sachet, a tablet or a capsule.

"Administration" refers generally to introducing the dosage form to a use environment, either by placing the dosage form in an in vitro dissolution medium or by ingestion by an animal so as to enter the in vivo environment of the GI tract.

As defined herein, the term "use environment" can be either the in vivo environment of the GI tract of an animal, such as a mammal and particularly a human, or the in vitro environment of a pH 6.0 $Na_2HPO_4$ buffer test medium as described in Example 5.

The term "mammal" is an individual animal that is a member of the taxonomic class Mammalia. The class Mammalia includes, for example, humans, monkeys, chimpanzees, gorillas, cattle, swine, horses, sheep, dogs, cats, mice and rats.

In the present invention, the preferred mammal is a human.

The dosage forms of the present invention provide better toleration of administered azithromycin, by raising pH in the stomach to a level sufficient to substantially reduce the release rate, or dissolution rate, of azithromycin in the stomach and thereby reduce the concentration of dissolved azithromycin in the stomach and in the duodenum. This reduction in the concentration of dissolved azithromycin in the stomach, and preferably in the duodenum, results in a decrease in the incidence, or frequency, of GI side effects when azithromycin is administered. Specifically, for a dosage form of the present invention, which comprise azithromycin and an effective amount of an alkalizing agent, the azithromycin release rate or dissolution rate for a dose of 1.5 gA to 7 gA, in the in vitro environment of the pH 6.0 $Na_2HPO_4$ buffer test medium of Example 5, should be (i) from 15 to 55 wt % of said azithromycin in said dosage form at 0.25 hour but no more than 1.1 gA; (ii) from 30 to 75 wt % of said azithromycin in said dosage form at 0.5 hour but no more than 1.5 gA, and preferably no more than 1.3 gA; and (iii) greater than 50 wt % of said azithromycin in said dosage form at 1 hour after administration to the buffer test medium. For doses below 1.5 gA, such as pediatric doses, the dose should be scaled up to 2 gA and then evaluated using this in vitro test.

The term "gA" refers to grams of active azithromycin, meaning the non-salt, non-hydrated azithromycin macrolide molecule having a molecular weight of 749 g/mol.

The present dosage forms provide a relative degree of improvement in toleration of administered azithromycin of at least 1.1 as compared to an equivalent immediate release dosage form. Preferably, the relative degree of improvement in toleration is at least about 1.25. More preferably, the relative improvement in toleration is at least about 1.5. Even more preferably, the relative improvement in toleration is at least about 2.0. Most preferably, the relative improvement in toleration is at least about 3.0.

In a preferred embodiment, the present dosage forms also maintain an appropriate level of bioavailability by not significantly lowering the azithromycin release rate and/or dissolution rate of administered azithromycin in the duodenum or distal to the duodenum. Typically, the present dosage forms provide a bioavailability of at least 60%, more preferably at least 70%, even more preferably at least 80%, and most preferably at least 90% relative to the control composition.

Alkalizing agents of the present invention raise the pH of acidic aqueous solutions and include, for example, antacids as well as other pharmaceutically acceptable (1) organic and inorganic bases, (2) salts of strong organic and inorganic acids, (3) salts of weak organic and inorganic acids, and (4) buffers.

Examples of such alkalizing agents include, but are not limited to, aluminum salts such as magnesium aluminum silicate; magnesium salts such as magnesium carbonate, magnesium trisilicate, magnesium aluminum silicate, magnesium stearate; calcium salts such as calcium carbonate; bicarbonates such as calcium bicarbonate and sodium bicarbonate; phosphates such as monobasic calcium phosphate, dibasic calcium phosphate, dibasic sodium phosphate, tribasic sodium phosphate (TSP), dibasic potassium phosphate, tribasic potassium phosphate; metal hydroxides such as aluminum hydroxide, sodium hydroxide and magnesium hydroxide; metal oxides such as magnesium oxide; N-methyl glucamine; arginine and salts thereof; amines such as monoethanolamine, diethanolamine, triethanolamine, and tris(hydroxymethyl)aminomethane (TRIS); and combinations thereof.

Preferably, the alkalizing agent is TRIS, magnesium hydroxide, magnesium oxide, dibasic sodium phosphate, TSP, dibasic potassium phosphate, tribasic potassium phosphate or a combination thereof. More preferably, the alkalizing agent is a combination of TSP and magnesium hydroxide.

When the alkalizing agent comprises TSP, it is preferred that the TSP be anhydrous.

The minimum amount of alkalizing agent suitable to constitute an "effective amount" is that amount which would provide a relative degree of improvement in toleration of at least 1.1.

This suitable amount of alkalizing agent can be readily determined by performing an in vitro ladder study of azithromycin dissolution rates by titrating a solution of a fixed dose of azithromycin with 0.1N HCl and increasing amounts of an alkalizing agent or combinations of alkalizing agents as described in Example 1.

For dosage forms containing azithromycin multiparticulates, an effective amount of an alkalizing agent, is that amount which, when titrated using an in vitro titration test against 0.1 N HCl, which simulates gastric fluid in the fed state, as described in Example 1, maintains a pH of about 5, or more, for at least about 10 minutes, and more preferably a pH of about 6, or more, for a period of about 10 minutes. Even more preferably, the alkalizing agent should maintain a pH of about 6 or more for about 20 minutes or more.

For azithromycin immediate release dosage forms, an effective amount of an alkalizing agent, is that amount which, when titrated using an in vitro titration test against 0.1 N HCl, as described in Example 1, maintains a pH of about 6.4, or more, for at least about 10 minutes, and more preferably for at least about 30 minutes.

Alternatively, an effective amount of an alkalizing agent can be determined in the following in vitro test. First, a 20-mL sample of 0.1 N HCl is placed in an appropriate container. Second, the candidate alkalizing agent is added to 60 mL of water. The so-formed alkalizing agent solution is then added to the 20-mL sample of 0.1 N HCl and the pH of the resulting solution is monitored over time. When the azithromycin is in the form of sustained-release multiparticulates, an effective amount of alkalizing agent is one such that the pH of the solution is at least 5, preferably at least 6, and more preferably at least 7. When the azithromycin is in an immediate release formulation, an effective amount of alkalizing agent is one such that the pH of the solution is at least 6.4, preferably at least 7.5, and more preferably at least 8.

An alkalizing agent of the present invention is administered contiguously with the administration of a dose of azithromycin. As used herein, the term "contiguously" means that the alkalizing agent is administered before, concurrent with or after the azithromycin within a period of time sufficient to slow the rate of release of azithromycin in the stomach and lower the concentration of dissolved azithromycin in the duodenum. For example, when administering azithromycin in a multiparticulate form, the alkalizing agent should be administered, between about 20 minutes before and about 10 minutes after administering the azithromycin. For an azithromycin immediate release dosage form, the alkalizing agent should be administered concurrently with the azithromycin or up to about 20 minutes before administering the azithromycin.

Preferably, the alkalizing agent is administered concurrently with the administration of the azithromycin.

The alkalizing agent can be mixed with the azithromycin dosage form as an integral part of a tablet, capsule, or preferably in a powder mixture if the controlled-release form is a powder for oral suspension.

The alkalizing agent may be in the same dosage form as is the azithromycin, the alkalizing agent may be contained in a vehicle used to administer the azithromycin, and/or the alkalizing agent can be administered separately from the azithromycin.

Wherein the azithromycin dosage form contains at least a portion of the alkalizing agent, the azithromycin dosage form can be any oral dosage form such as a suspension, tablet, capsule or sachet.

Wherein the alkalizing agent is at least partially contained in the vehicle, the azithromycin dosage form can be a sachet, powder for oral suspension, tablet or capsule.

Where the alkalizing agent is at least partially administered separately from the azithromycin, the alkalizing agent can be in any oral dosage form such as a liquid, suspension, tablet, capsule or sachet.

As used herein, "azithromycin" means all amorphous and crystalline forms of azithromycin including all polymorphs, isomorphs, clathrates, salts, solvates and hydrates of azithromycin, as well as anhydrous azithromycin.

Preferably, the azithromycin of the present invention is azithromycin dihydrate which is disclosed in U.S. Pat. No. 6,268,489 B1.

In alternate embodiments of the present invention, the azithromycin comprises a non-dihydrate azithromycin, a mixture of non-dihydrate azithromycins, or a mixture of azithromycin dihydrate and non-dihydrate azithromycins. Examples of suitable non-dihydrate azithromycins include, but are not limited to, alternate crystalline forms B, D, E, F, G, H, J, M, N, O, P, Q and R.

Azithromycin form B, which is a hygroscopic hydrate of azithromycin, is disclosed in U.S. Pat. No. 4,474,768.

Azithromycin forms D, E, F, G, H, J, M, N, O, P, Q and R are disclosed in U.S. patent application Ser. No. (USSN) 10/152,106, which published on Aug. 28, 2003 as U.S. Patent Application Publication No. 20030162730 A1.

Forms B, F, G, H, J, M, N, O, and P belong to Family I azithromycin and belong to a monoclinic $P2_1$ space group with cell dimensions of a=16.3±0.3 Å, b= 16.2±0.3 Å, c=18.4±0.3 Å and beta=109±2°.

Form F azithromycin is an azithromycin ethanol solvate of the formula $C_{38}H_{72}N_2O_{12} \cdot H_2O \cdot 0.5C_2H_5OH$ in the single crystal structure, specifically, being an azithromycin monohydrate hemi-ethanol solvate. Form F is further characterized as containing 2–5% water and 1–4% ethanol by weight in powder samples. The single crystal of form F is crystallized in a monoclinic space group, P2$_1$, with the asymmetric unit containing two azithromycin, two waters, and one ethanol, as a monohydrate/hemi-ethanolate. It is isomorphic to all Family I azithromycin crystalline forms. The theoretical water and ethanol contents are 2.3 and 2.9 wt %, respectively.

Form G azithromycin is of the formula $C_{38}H_{72}N_2O_{12}$·1.5H$_2$O in the single crystal structure, being azithromycin sesquihydrate. Form G is further characterized as containing 2.5–6 wt % water and <1 wt % organic solvent(s) by weight in powder samples. The single crystal structure of form G consists of two azithromycin molecules and three water molecules per asymmetric unit. This corresponds to a sesquihydrate with a theoretical water content of 3.5 wt %. The water content of powder samples of form G ranges from about 2.5 to about 6 wt %. The total residual organic solvent is less than 1 wt % of the corresponding solvent used for crystallization.

Form H azithromycin is of the formula $C_{38}H_{72}N_2O_{12}$·H$_2$O·0.5C$_3$H$_8$O$_2$ being azithromycin monohydrate hemi-1,2 propanediol solvate. Form H is a monohydrate/hemi-propylene glycol solvate of azithromycin free base.

Form J azithromycin is of the formula $C_{38}H_{72}N_2O_{12}$·H$_2$O·0.5C$_3$H$_7$OH in the single crystal structure, being azithromycin monohydrate hemi-n-propanol solvate. Form J is further characterized as containing 2–5 wt % water and 1–5 wt % n-propanol by weight in powder samples. The calculated solvent content is about 3.8 wt % n-propanol and about 2.3 wt % water.

Form M azithromycin is an isopropanol solvate of azithromycin of the formula $C_{38}H_{72}N_2O_{12}$·H$_2$O·0.5C$_3$H$_7$OH, specifically, being azithromycin monohydrate hemi-isopropanol solvate. Form M is further characterized as containing 2–5 wt % water and 1–4 wt % 2-propanol by weight in powder samples. The single crystal structure of form M would be a monohydrate/hemi-isopropranolate.

Form N azithromycin is a mixture of isomorphs of Family I. The mixture may contain variable percentages of isomorphs F, G, H, J, M and others, and variable amounts of water and organic solvents, such as ethanol, isopropanol, n-propanol, propylene glycol, acetone, acetonitrile, butanol, pentanol, etc. The weight percent of water can range from 1–5.3 wt % and the total weight percent of organic solvents can be 2–5 wt % with each solvent making up 0.5 to 4 wt %.

Form O azithromycin is of the formula $C_{38}H_{72}N_2O_{12}$·0.5H$_2$O·0.5C$_4$H$_9$OH, being a hemihydrate hemi-n-butanol solvate of azithromycin free base by single crystal structural data.

Form P azithromycin is of the formula $C_{38}H_{72}N_2O_{12}$·H$_2$O·0.5C$_5$H$_{12}$O, being azithromycin monohydrate hemi-n-pentanol solvate.

Form Q azithromycin is of the formula $C_{38}H_{72}N_2O_{12}$·H$_2$O·0.5C$_4$H$_8$O, being azithromycin monohydrate hemi-tetrahydrofuran solvate. It contains about 4 wt % water and about 4.5 wt % THF.

Forms D, E and R belong to Family II azithromycin and belong to an orthorhombic P2$_1$ 2$_1$2$_1$ space group with cell dimensions of a=8.9±0.4 Å, b= 12.3±0.5 Å and c=45.8±0.5 Å. Form Q is distinct from Families I and II.

Form D azithromycin is of the formula $C_{38}H_{72}N_2O_{12}$·H$_2$O·C$_6$H$_{12}$ in its single crystal structure, being azithromycin monohydrate monocyclohexane solvate. Form D is further characterized as containing 2–6 wt % water and 3–12 wt % cyclohexane by weight in powder samples. From single crystal data, the calculated water and cyclohexane content of form D is 2.1 and 9.9 wt %, respectively.

Form E azithromycin is of the formula $C_{38}H_{72}N_2O_{12}$·H$_2$O·C$_4$H$_8$O, being azithromycin monohydrate mono-tetrahydrofuran solvate. Form E is a monohydrate and mono-THF solvate by single crystal analysis.

Form R azithromycin is of the formula $C_{38}H_{72}N_2O_{12}$·H$_2$O·C$_5$H$_{12}$O, being azithromycin monohydrate mono-methyl tert-butyl ether solvate. Form R has a theoretical water content of 2.1 wt % and a theoretical methyl tert-butyl ether content of 10.3 wt %.

Both Family I and Family II isomorphs are hydrates and/or solvates of azithromycin. The solvent molecules in the cavities have a tendency to exchange between solvent and water under specific conditions. Therefore, the solvent/water content of the isomorphs may vary to a certain extent.

Other examples of non-dihydrate azithromycin include, but are not limited to, an ethanol solvate of azithromycin or an isopropanol solvate of azithromycin. Examples of such ethanol and isopropanol solvates of azithromycin are disclosed in U.S. Pat. No. 6,365,574, by Singer et al., titled "Ethanolate of azithromycin, process for manufacture, and pharmaceutical compositions thereof", U.S. Pat. No. 6,245,903, by Karimian et al., titled "Azithromycin monohydrate isopropanol clatharate and methods for the manufacture thereof" or in U.S. Ser. No. 10/152,106.

Additional examples of non-dihydrate azithromycin include, but are not limited to, azithromycin monohydrate as disclosed in U.S. Patent Application Publication Nos. 20010047089 which published on Nov. 29, 2001, and 20020111318 which published on Aug. 15, 2002, as well as, International Application Publication Numbers WO 01/00640, WO 01/49697, WO 02/10181 and WO 02/42315.

Further examples of non-dihydrate azithromycin include, but are not limited to, anhydrous azithromycin as disclosed in U.S. Patent Application Publication No. 20030139583 which published on Jul. 24, 2003 and U.S. Pat. No. 6,528,492.

Examples of suitable azithromycin salts include, but are not limited to, the azithromycin salts as disclosed in U.S. Pat. No. 4,474,768.

Preferably, at least 70 wt % of the azithromycin in the multiparticulate is crystalline. More preferably, at least 80 wt % of the azithromycin is crystalline. Even more preferably, at least 90 wt % of the azithromycin is crystalline. Most preferably, at least 95 wt % of the azithromycin is crystalline. Crystalline azithromycin is preferred since it is more chemically and physically stable than the amorphous form or dissolved azithromycin.

The crystallinity of the azithromycin may be determined using Powder X Ray Diffraction (PXRD) analysis. In an exemplary procedure, PXRD analysis may be performed on a Bruker AXS D8 Advance diffractometer. In this analysis, samples of about 500 mg are packed in Lucite sample cups and the sample surface smoothed using a glass microscope slide to provide a consistently smooth sample surface that is level with the top of the sample cup. Samples are spun in the φ plane at a rate of 30 rpm to minimize crystal orientation effects. The X-ray source (S/B KCu$_\alpha$, λ=1.54 Å) is operated at a voltage of 45 kV and a current of 40 mA. Data for each sample are collected over a period of about 20 to about 60 minutes in continuous detector scan mode at a scan speed of about 1.8 seconds/step to about 12 seconds/step and a step size of 0.02°/step. Diffractograms are collected over the 2θ range of about 4° to 30°.

The crystallinity of the test sample is determined by comparison with two or more calibration standards consisting of physical mixtures of crystalline azithromycin and carrier. Each physical mixture is blended together about 15 minutes on a Turbula mixer. Using the instrument software, the area under the diffractogram curve is integrated over the 2θ range using a linear baseline. This integration range includes as many drug-specific peaks as possible while excluding carrier-related peaks. A linear calibration curve of percent crystalline drug versus the area under the diffractogram curve is generated from the calibration standards. The crystallinity of the test sample is then determined using these calibration results and the area under the curve for the test sample. Results are reported as a mean percent of azithromycin crystallinity (by crystal mass).

The azithromycin used herein comprises azithromycin particles which are contained in a dosage form that, absent the alkalizing agent of the present invention, is either an immediate release or a sustained release dosage form. As defined herein, the term "azithromycin particles" means the azithromycin may be in the form of a powder or of granules which were previously formed from azithromycin powder and, optionally, at least one pharmaceutically acceptable excipient.

Immediate release dosage forms are those forms wherein at least 75% of their azithromycin is released or dissolved within about one-half hour after administration. Such immediate release dosage forms include tablets, capsules, multiparticulates, powders for oral suspension and sachets of azithromycin. Examples of immediate release dosage forms include, but are not limited to, commercially available Zithromax® tablets, capsules, oral suspensions, or single-dose packets for oral suspension (Pfizer Inc., New York, N.Y.) or the multiparticulate control dosage form which is described herein in Example 2.

Sustained release dosage forms are those forms that release azithromycin more slowly than immediate release dosage forms. Such sustained release dosage forms include, but are not limited to, tablets, capsules, multiparticulates, powders for oral suspension and sachets of azithromycin.

Examples of azithromycin sustained release dosage forms, which are suitable for use in the present invention, include, but are not limited to, the sustained release dosage forms described in U.S. Pat. No. 6,068,859.

Preferably, the azithromycin used in the present invention is contained in a multiparticulate which comprises azithromycin and a pharmaceutically acceptable carrier.

Multiparticulates are well-known dosage forms that comprise a multiplicity of drug-containing particles whose totality represents the intended therapeutically useful dose of a drug. When taken orally, multiparticulates generally disperse freely in the gastrointestinal tract, exit relatively rapidly and reproducibly from the stomach and maximize absorption. See, for example, *Multiparticulate Oral Drug Delivery* (Marcel Dekker, 1994), and *Pharmaceutical Pelletization Technology* (Marcel Dekker, 1989).

Multiparticulates are often used to provide sustained release of a drug. One problem when formulating a sustained release multiparticulate is setting the release rate of the drug. The release rate of the drug depends on a variety of factors, including the carriers used to form the multiparticulate and the amount of drug in the multiparticulate. It is desired to provide carriers for a multiparticulate which allow the release rate of the drug from the multiparticulate to be controlled over a wide range of release rates, so that the same matrix materials in different proportions may be used to provide slow or fast drug release as desired. To achieve this result, the release rate of the drug should change significantly in response to relatively small changes in the proportions of the respective carriers in the multiparticulate.

The term "multiparticulates" is intended to embrace a dosage form comprising a multiplicity of particles whose totality represents the intended therapeutically useful dose of azithromycin. The term is intended to refer broadly to small particles regardless of their composition or the manner in which they are formed. The particles are small enough so that the particles travel with GI fluids to disperse throughout the GI tract shortly after ingestion. The particles generally are of a mean diameter from about 40 to about 3000 μm, preferably from about 50 to about 1000 μm, and most preferably from about 100 to about 300 μm. Preferably, the azithromycin makes up about 5 wt % to about 90 wt % of the total weight of the multiparticulate. More preferably, the azithromycin makes up about 10 wt % to about 80 wt % of the multiparticulate, and even more preferably, at least about 30 wt % to about 60 wt % of the multiparticulate.

While the multiparticulates can have any shape and texture, it is preferred that they be spherical, with a smooth surface texture. These physical characteristics lead to excellent flow properties, improved "mouth feel," ease of swallowing and ease of uniform coating, if required.

Such multiparticulates of azithromycin are particularly suitable for administration of single doses of the drug inasmuch as a relatively large amount of the drug can be delivered at a controlled rate over a relatively long period of time. Multiparticulates suitable for use in the present invention are disclosed in U.S. Pat. No. 6,068,859, including multiparticulates made by extrusion/spheronization, wax granulation, spray-drying, and spray-coating.

The multiparticulate's carrier comprises at least one pharmaceutically acceptable excipient which functions as a matrix for the multiparticulate or to control the rate of release of azithromycin from the multiparticulate, or both.

All references to "acid and/or ester substituents" herein are intended to mean carboxylic acid, sulfonic acid, and phosphoric acid substituents or carboxylic acid ester, sulfonyl ester, or phosphate ester substituents, respectively. As described in detail below, azithromycin may react with acid or ester substituents on an excipient to form azithromycin esters.

Azithromycin can potentially react with carriers, and optional excipients, which have acidic or ester groups to form esters of azithromycin. Carriers and excipients may be characterized as having "low reactivity," "medium reactivity," and "high reactivity" to form azithromycin esters.

Examples of low reactivity carriers and optional excipients include long-chain alcohols, such as stearyl alcohol, cetyl alcohol, and polyethylene glycol; poloxamers (block copolymers of ethylene oxide and propylene oxide, such as poloxamer 188, poloxamer 237, poloxamer 338, and poloxamer 407); ethers, such as polyoxyethylene alkyl ethers; ether-substituted cellulosics, such as microcrystalline cellulose, hydroxypropyl cellulose, hydroxypropyl methyl cellulose, and ethylcellulose; sugars such as glucose, sucrose, xylitol, sorbitol, and maltitol; and salts such as sodium chloride, potassium chloride, lithium chloride, calcium chloride, magnesium chloride, sodium sulfate, potassium sulfate, sodium carbonate, magnesium sulfate, and potassium phosphate.

Moderate reactivity carriers and optional excipients often contain acid or ester substituents, but relatively few as compared to the molecular weight of the carrier or optional excipient. Examples include long-chain fatty acid esters, such as glyceryl monooleate, glyceryl monostearate, glyceryl palmitostearate, polyethoxylated castor oil derivatives, hydrogenated vegetable oils, glyceryl dibehenate, and mixtures of mono-, di-, and tri-alkyl glycerides; glycolized fatty acid esters, such as polyethylene glycol stearate and polyethylene glycol distearate; polysorbates; and waxes, such as Carnauba wax and white and yellow beeswax. Glyceryl behenate, as defined herein, comprises glyceryl monobehenate, glyceryl dibehenate, glyceryl tribehenate, or a mixture of any two or all three of said glyceryl mono-, di- and tribehenates.

Highly reactive carriers and optional excipients usually have several acid or ester substituents or low molecular weights. Examples include carboxylic acids such as stearic acid, benzoic acid, citric acid, fumaric acid, lactic acid, and maleic acid; short to medium chain fatty-acid esters, such as isopropyl palmitate, isopropyl myristate, triethyl citrate, lecithin, triacetin, and dibutyl sebacate; ester-substituted cellulosics, such as cellulose acetate, cellulose acetate phthalate, hydroxypropyl methyl cellulose phthalate, cellulose acetate trimellitate, and hydroxypropyl methyl cellulose acetate succinate; and acid or ester functionalized polymethacrylates and polyacrylates. Generally, the acid/ester concentration on highly reactive carriers and optional excipients is so high that if these carriers and optional excipients come into direct contact with azithromycin in the formulation, unacceptably high concentrations of azithromycin esters form during processing or storage of the composition. Thus, such highly reactive carriers and optional excipients are preferably only used in combination with a carrier or optional excipient with lower reactivity so that the total amount of acid and ester groups on the carrier and optional excipients used in the multiparticulate is low.

To obtain multiparticulates with an acceptable amount of azithromycin esters (i.e. less than about 1 wt %), there is a trade-off relationship between the concentration of acid and ester substituents on the carrier and the crystallinity of azithromycin in the multiparticulate. The greater the crystallinity of azithromycin in the multiparticulate, the greater the degree of the carrier's acid/ester substitution may be to obtain a multiparticulate with acceptable amounts of azithromycin esters. This relationship may be quantified by the following mathematical expression:

$$[A] \leq 0.04/(1-x) \tag{I}$$

where [A] is the total concentration of acid/ester substitution on the carrier and optional excipients in meq/g azithromycin and is less than or equal to 2 meq/g, and x is the weight fraction of the azithromycin in the composition that is crystalline. When the carrier and optional excipients comprises more than one excipient, the value of [A] refers to the total concentration of acid/ester substitution on all the excipients that make up the carrier and optional excipients, in units of meq/g azithromycin.

For more preferable multiparticulates having less than about 0.5 wt % azithromycin esters, the azithromycin, carrier, and optional excipients will satisfy the following expression:

$$[A] \leq 0.02/(1-x). \tag{II}$$

For more preferable multiparticulates having less than about 0.2 wt % azithromycin esters, the azithromycin, carrier, and optional excipients will satisfy the following expression:

$$[A] \leq 0.008/(1-x). \tag{III}$$

For most preferable multiparticulates having less than about 0.1 wt % azithromycin esters, the azithromycin, carrier, and optional excipients will satisfy the following expression:

$$[A] \leq 0.004/(1-x). \tag{IV}$$

From the foregoing mathematical expressions (I)–(IV) the trade-off between the carrier's and optional excipient's degree of acid/ester substitution and the crystallinity of azithromycin in the composition can be determined.

Carriers used in the multiparticulates of the present invention will generally make up about 10 wt % to about 95 wt % of the multiparticulate, preferably about 20 wt % to about 90 wt, and more preferably about 40 wt % to about 70 wt %, based on the total mass of the multiparticulate.

To minimize the potential for changes in the physical characteristics of the multiparticulates over time, especially when stored at elevated temperatures, it is preferred that the carrier be solid at a temperature of at least about 40° C. More preferably, the carrier should be solid at a temperature of at least about 50° C. and even more preferably of at least about 60° C.

In one embodiment, the carrier forms a solid solution with one or more optional excipients, meaning that the carrier and one or more optional excipients form a single thermodynamically stable phase. In such cases, excipients that are not solid at a temperature of at least 40° C. can be used, provided the carrier/excipient mixture is solid at a temperature of at least 40° C. This will depend on the melting point of the excipients used and the relative amount of carrier included in the composition.

In another embodiment, the carrier and one or more optional excipients do not form a solid solution, meaning that the carrier and one or more optional excipients form two or more thermodynamically stable phases. In such cases, the carrier/excipient mixture may be entirely molten at the processing temperatures used to form multiparticulates or one material may be solid while the other(s) are molten, resulting in a suspension of one material in the molten mixture.

When the carrier and one or more optional excipients do not form a solid solution but a solid solution is desired, for example, to obtain a specific controlled-release profile, an additional excipient may be included in the composition to produce a solid solution comprising the carrier, the one or more optional excipients, and the additional excipient. For example, it may be desirable to use a carrier comprising microcrystalline wax and a poloxamer to obtain a multiparticulate with the desired release profile. In such cases a solid solution is not formed, in part due to the hydrophobic nature of the microcrystalline wax and the hydrophilic nature of the poloxamer. By including a small amount of a third excipient, such as stearyl alcohol, in the formulation, a solid solution can be obtained, resulting in a multiparticulate with the desired release profile.

Examples of carriers suitable for use in the multiparticulates of the present invention include waxes, such as synthetic wax, microcrystalline wax, paraffin wax, Carnauba wax, and beeswax; glycerides, such as glyceryl monooleate, glyceryl monostearate, glyceryl palmitostearate, polyethoxylated castor oil derivatives, hydrogenated vegetable oils, a glyceryl behenate, glyceryl tristearate, glyceryl tripalmitate; long-chain alcohols, such as stearyl alcohol, cetyl alcohol, and polyethylene glycol; and mixtures thereof.

Preferably, the carrier comprises a glyceride having at least one alkylate substituent of 16 or more carbon atoms. More preferably, the carrier comprises a glyceryl behenate.

In an alternate embodiment, the multiparticulates are in the form of a non-disintegrating matrix. By "non-disintegrating matrix" is meant that at least a portion of the carrier does not dissolve or disintegrate after introduction of the multiparticulates to an aqueous use environment. In such cases, the azithromycin and optionally a portion of one or more of the carriers, for example, a dissolution enhancer, are removed from the multiparticulate by dissolution. At least a portion of the carrier does not dissolve or disintegrate and is excreted when the use environment is in vivo, or remains suspended in a test solution when the use environment is in vitro. In this aspect, it is preferred that at least a portion of the carrier have a low solubility in the aqueous use environment. Preferably, the solubility of at least a portion of the carrier in the aqueous use environment is less than about 1 mg/mL, more preferably less than about 0.1 mg/mL, and most preferably less than about 0.01 mg/ml. Examples of suitable low-solubility carriers include waxes, such as synthetic wax, microcrystalline wax, paraffin wax, Carnauba wax, and beeswax; glycerides, such as glyceryl monooleate, glyceryl monostearate, glyceryl palmitostearate, glyceryl behenates, glyceryl tristearate, glyceryl tripalmitate; and mixtures thereof.

In a preferred embodiment of the present invention, the azithromycin multiparticulates of the present invention comprise azithromycin, a carrier and a dissolution enhancer. The carrier and the dissolution enhancer function as a matrix for the multiparticulate or to control the azithromycin release rate from the multiparticulate, or both. The term "dissolution enhancer" means an excipient, which when included in the multiparticulates, results in a faster rate of release of azithromycin than that provided by a control multiparticulate containing the same amount of azithromycin without the dissolution enhancer. Generally, the rate of release of azithromycin from the multiparticulate increases with increasing amounts of dissolution enhancers. Such agents generally have a high water solubility and are often surfactants or wetting agents that can promote solubilization of other excipients in the composition. Typically, the weight percentage of dissolution enhancer present in the multiparticulate is less than the weight percentage of carrier present in the multiparticulate.

The multiparticulates of the present invention comprise about 20 to about 75 wt % azithromycin, about 25 to about 80 wt % of a carrier, and about 0.1 to about 30 wt % of a dissolution enhancer based on the total mass of the multiparticulate. In a preferred embodiment, the multiparticulate comprises 35 to 55 wt % azithromycin, 40 to 65 wt % of a carrier, and 1 to 15 wt % dissolution enhancer.

Examples of suitable dissolution enhancers include, but are not limited to, alcohols such as stearyl alcohol, cetyl alcohol, and polyethylene glycol; surfactants, such as poloxamers (polyoxyethylene polyoxypropylene copolymers, including poloxamer 188, poloxamer 237, poloxamer 338, and poloxamer 407), docusate salts, polyoxyethylene alkyl ethers, polyoxyethylene castor oil derivatives, polyoxyethylene sorbitan fatty acid esters, sorbitan esters, alkyl sulfates (such as sodium lauryl sulfate), polysorbates, and polyoxyethylene alkyl esters; ether-substituted cellulosics, such as hydroxypropyl cellulose and hydroxypropyl methyl cellulose; sugars such as glucose, sucrose, xylitol, sorbitol, and maltitol; salts such as sodium chloride, potassium chloride, lithium chloride, calcium chloride, magnesium chloride, sodium sulfate, potassium sulfate, sodium carbonate, magnesium sulfate, and potassium phosphate; amino acids such as alanine and glycine; and mixtures thereof. Preferably, the dissolution enhancer comprises a surfactant.

More preferably, the dissolution enhancer comprises a poloxamer. Poloxamers are a series of closely related block copolymers of ethylene oxide and propylene oxide that have no acid or ester substituents. This being the case, large amounts of poloxamers, as much as 30 wt % can be used in a multiparticulate formulation and still meet the target value of less than about 0.13 meq/g of azithromycin. Even more preferably, the poloxamer is Poloxamer 407 which is described in the exemplification herein.

In this embodiment wherein the multiparticulate further comprises a dissolution enhancer, it is further preferred that the carrier is selected from the group consisting of waxes, such as synthetic wax, microcrystalline wax, paraffin wax, Carnauba wax, and beeswax; glycerides, such as glyceryl monooleate, glyceryl monostearate, glyceryl palmitostearate, polyethoxylated castor oil derivatives, hydrogenated vegetable oils, glyceryl mono-, di- or tribehenates, glyceryl tristearate, glyceryl tripalmitate; and mixtures thereof.

The azithromycin present in the multiparticulate has been found to be particularly reactive with dissolution enhancers. As a result, the concentration of acid and ester substituents on the dissolution enhancer must be kept low to keep the formation of azithromycin esters at acceptably low levels.

From the standpoint of reactivity to form azithromycin esters, the dissolution enhancers preferably have a concentration of acid/ester substituents of less than about 0.13 meq/g azithromycin present in the composition. Preferably, the dissolution enhancer has a concentration of acid/ester substituents of less than about 0.10 meq/g azithromycin, more preferably less than about 0.02 meq/g azithromycin, even more preferably less than about 0.01 meq/g, and most preferably less than about 0.002 meq/g.

In addition to having low concentrations of acid and ester substituents, the dissolution enhancer should generally be hydrophilic, such that the rate of release of azithromycin from the multiparticulate increases as the concentration of dissolution enhancer in the multiparticulate increases.

Further description of suitable dissolution enhancers and selection of appropriate excipients for azithromycin multiparticulates are disclosed in U.S. patent application Ser. No. 11/003,853, filed concurrently herewith.

In a more preferred embodiment, the multiparticulates of the present invention comprise (a) azithromycin; (b) a glyceride carrier having at least one alkylate substituent of 16 or more carbon atoms; and (c) a poloxamer dissolution enhancer. The choice of these particular carrier excipients allows for precise control of the release rate of the azithromycin over a wide range of release rates. Small changes in the relative amounts of the glyceride carrier and the poloxamer result in large changes in the release rate of the drug. This allows the release rate of the drug from the multiparticulate to be precisely controlled by selecting the proper ratio of drug, glyceride carrier and poloxamer. These materials have the further advantage of releasing nearly all of the drug from the multiparticulate. Such multiparticulates are disclosed more fully in U.S. patent application Ser. No. 11/004,168, filed concurrently herewith.

Additional optional excipients may also be included in the azithromycin multiparticulates. For example, agents that inhibit or delay the release of azithromycin from the multiparticulates can also be included in the carrier. Such dissolution-inhibiting agents are generally hydrophobic. Examples of dissolution-inhibiting agents include hydrocarbon waxes, such as microcrystalline and paraffin wax.

Another useful class of excipients is materials that are used to adjust the viscosity of the molten feed used to form the multiparticulates, for example, by a melt-congeal process. Such viscosity-adjusting excipients will generally make up 0 to 25 wt % of the multiparticulate, based on the total mass of the multiparticulate. The viscosity of the molten feed is a key variable in obtaining multiparticulates with a narrow particle size distribution. For example, when a spinning-disc atomizer is employed, it is preferred that the viscosity of the molten mixture be at least about 1 centipoise (cp) and less than about 10,000 cp, more preferably at least 50 cp and less than about 1000 cp. If the molten mixture has a viscosity outside these preferred ranges, a viscosity-adjusting carrier can be added to obtain a molten mixture within the preferred viscosity range. Examples of viscosity-reducing excipients include stearyl alcohol, cetyl alcohol, low molecular weight polyethylene glycol (e.g., less than about 1000 daltons), isopropyl alcohol, and water. Examples of viscosity-increasing excipients include microcrystalline wax, paraffin wax, synthetic wax, high molecular weight polyethylene glycols (e.g., greater than about 5000 daltons), ethyl cellulose, hydroxypropyl cellulose, hydroxypropyl methyl cellulose, methyl cellulose, silicon dioxide, microcrystalline cellulose, magnesium silicate, sugars, and salts.

Other excipients may be added to reduce the static charge on the multiparticulates; examples of such anti-static agents include talc and silicon dioxide. Flavorants, colorants, and other excipients may also be added in their usual amounts for their usual purposes.

In addition to the multiparticulates and an alkalizing agent, the azithromycin dosage form of the present invention may further comprise one or more additional excipients.

For example, surfactants may be included in the dosage form. Examples of suitable surfactants include fatty acid and alkyl sulfonates; commercial surfactants such as benzalkonium chloride (HYAMINE® 1622, available from Lonza, Inc., Fairlawn, N.J.); dioctyl sodium sulfosuccinate (DOCUSATE SODIUM™, available from Mallinckrodt Specialty Chemicals, St. Louis, Mo.); polyoxyethylene sorbitan fatty acid esters (TWEEN®, available from ICI Americas Inc., Wilmington, Del.; LIPOSORB® P-20, available from Lipochem Inc., Patterson N.J.; CAPMUL® POE-0, available from Abitec Corp., Janesville, Wis.); and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate at which the multiparticulates disperse when administered to the use environment.

Conventional matrix materials, fillers, diluents, lubricants, preservatives, thickeners, anticaking agents, disintegrants, or binders may also be included in the dosage form.

Examples of matrix materials, fillers, or diluents include lactose, mannitol, xylitol, microcrystalline cellulose, dibasic calcium phosphate and starch.

Examples of disintegrants include sodium starch glycolate, sodium alginate, carboxymethylcellulose sodium, methyl cellulose, croscarmellose sodium and cross linked forms of polyvinyl pyrrolidone, also known as crospovidone.

Examples of binders include methyl cellulose, microcrystalline cellulose, starch, and gums such as guar gum, and tragacanth.

Examples of lubricants include magnesium stearate, calcium stearate, and stearic acid.

Examples of preservatives include sulfites (an antioxidant), benzalkonium chloride, methyl paraben, propyl paraben, benzyl alcohol and sodium benzoate.

Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide.

Examples of anticaking agents or fillers include colloidal silicon oxide and lactose.

Other conventional excipients may be employed in the compositions of this invention, including those excipients well-known in the art. Generally, excipients such as pigments, lubricants, flavorants, and so forth may be used for customary purposes and in typical amounts without adversely affecting the properties of the compositions.

In one embodiment, the dosage form is in the form of a tablet. The term "tablet" is intended to embrace compressed tablets, coated tablets, and other forms known in the art. See for example, *Remington's Pharmaceutical Sciences* (18th Ed. 1990). Upon administration to the use environment, the tablet rapidly disintegrates, allowing the multiparticulates to be dispersed in the use environment.

In one embodiment, the tablet comprises multiparticulates that have been mixed with a binder, disintegrants, or other excipients known in the art, and then formed into a tablet using compressive forces. Examples of binders include microcrystalline cellulose, starch, gelatin, polyvinyl pyrrolidinone, polyethylene glycol, and sugars such as sucrose, glucose, dextrose, and lactose. Examples of disintegrants include sodium starch glycolate, croscarmellose sodium, crospovidone, and sodium carboxymethyl cellulose. The tablet may also include an effervescent agent (acid-base combinations) that generates carbon dioxide when placed in the use environment. The carbon dioxide generated helps in disintegration of the tablet. Other excipients, such as those discussed above, may also be included in the tablet.

The multiparticulates, binder, and other excipients used in the tablet may be granulated prior to formation of the tablet. Wet- or dry-granulation processes, well known in the art, may be used, provided the granulation process does not change the release profile of the multiparticulates. Alternatively, the materials may be formed into a tablet by direct compression.

The compression forces used to form the tablet should be sufficiently high to provide a tablet with high strength, but not too high to damage the multiparticulates contained in the tablet. Generally, compression forces that result in tablets with a hardness of about 3 to about 10 kp are desired.

Alternatively, tablets, such as multilayered and osmotic coated tablets, may also be made using non-compression processes. In one embodiment, the tablet is formed by a lyophylization process. In this process the multiparticulates are mixed with an aqueous solution or paste of water-soluble excipients and placed into a mold. The water is then removed by lyophylization, resulting in a highly porous, fast dissolving tablet containing the multiparticulates. Examples of water-soluble excipients used in such tablets include gelatin, dextran, dextrin, polyvinyl pyrrolidone, polyvinyl alcohol, trehalose, xylitol, sorbitol and mannitol.

In another embodiment, the dosage form is in the form of a capsule, well known in the art. See *Remington's Pharmaceutical Sciences* (18th Ed. 1990). The term "capsule" is intended to embrace solid dosage forms in which the multiparticulates and optional excipients are enclosed in either a hard or soft, soluble container or shell. Upon administration to the use environment, the shell dissolves or disintegrates, releasing the contents of the capsule to the use environment. The hard gelatin capsule, typically made from gelatin, consists of two sections, one slipping over the other. The capsules are made by first blending the multiparticulates and optional excipients, such as those listed above. The ingredients may be granulated using wet- or dry-granulation techniques to improve the flow of the fill material. The capsules are filled by introducing the fill material into the longer end or body of the capsule and then slipping on the cap. For soft-gelatin capsules, the fill material may first be suspended in an oil or liquid prior to filling the capsule.

The dosage form may also be in the form of pills. The term "pill" is intended to embrace small, round solid dosage forms that comprise the multiparticulates mixed with a binder and other excipients as described above. Upon administration to the use environment, the pill rapidly disintegrates, allowing the multiparticulates to be dispersed therein.

In another embodiment, the multiparticulate dosage form is in the form of a powder or granules comprising the multiparticulates and other excipients as described above, that is then suspended in a liquid dosing vehicle, including an aqueous dosing vehicle, prior to dosing. Such dosage forms may be prepared by several methods. In one method, the powder is placed into a container and an amount of a liquid, such as water, is added to the container. The container is then mixed, stirred, or shaken to suspend the dosage form in the water. In another method, the multiparticulates and dosing vehicle excipients are supplied in two or more separate packages. The dosing vehicle excipients are first dissolved or suspended in a liquid, such as water, and then the multiparticulates are added to the liquid vehicle solution. Alternatively, the dosing vehicle excipients and multiparticulates, in two or more individual packages, can be added to the container first, water added to the container, and the container mixed or stirred to form a suspension.

Water is an example of a liquid that can be used to form the dosage form of the invention. Other liquids may also be used and are intended to be within the scope of the invention. Examples of suitable liquids include beverages, such as coffee, tea, milk, and various juices. Also included is water mixed with other excipients to help form the dosage form, including surfactants, thickeners, suspending agents, and the like.

The multiparticulate dosage form may also be in the form of a dosing straw or other such device that allows the patient to sip water or other liquid through the device, the device being designed to mix the liquid with the powdered or granular dosage form contained in the device.

The multiparticulate dosage form may also be in the form of a paste, slurry or suspension.

In one embodiment, the multiparticulate dosage form comprises azithromycin multiparticulates, an alkalizing agent and one or more optional excipients selected from a sweetener, an anticaking agent, a viscosity-enhancing agent and a flavorant. Preferably, the multiparticulate dosage form further comprises a sweetener, an anticaking agent, a viscosity-enhancing agent and a flavorant.

In an even more preferred embodiment of the present invention, the azithromycin multiparticulates are administered with the alkalizing agent TSP. The amount of TSP is preferably at least about 200 mg. More preferably the amount of TSP ranges from about 300 mg to about 400 mg. In another embodiment of the present invention TSP and magnesium hydroxide are both used as the alkalizing agent. The amount of magnesium hydroxide used is at least about 100 mg and preferably from about 200 mg to about 300 mg.

In a further preferred embodiment, the azithromycin dosage form comprises azithromycin multiparticulates, comprising about 45 to about 55 wt % azithromycin, about 43 to about 50 wt % glyceryl behenate and about 2 to about 5 wt % poloxamer, and an alkalizing agent comprising about 300 to about 400 mg TSP and about 200 to about 300 mg magnesium hydroxide.

In yet an even more preferred embodiment the azithromycin dosage form comprises azithromycin multiparticulates, comprising about 50 wt % azithromycin dihydrate, about 46 to about 48 wt % Compritol® 888 ATO, and about 2 to about 4 wt % Poloxamer 407, and an alkalizing agent comprising about 300 to about 400 mg TSP and about 200 to about 300 mg magnesium hydroxide. More preferably, said dosage form comprises about 47 wt % Compritol® 888 ATO and about 3 wt % Poloxamer 407. Compritol® 888 ATO and Poloxamer 407 are further described below in the Exemplification.

The multiparticulates of the present invention can be made by any known process that results in particles, containing azithromycin and a carrier, with the desired size and release rate characteristics for the azithromycin. Preferred processes for forming such multiparticulates include thermal-based processes, such as melt- and spray-congealing; liquid-based processes, such as extrusion spheronization, wet granulation, spray-coating, and spray-drying; and other granulation processes such as dry granulation and melt granulation.

The multiparticulates generally have a mean diameter of less than about 5000 μm, preferably less than 3000 μm, and most preferably less than about 1000 μm. In a preferred embodiment, the mean diameter of the multiparticulates ranges from about 40 to about 3000 μm, preferably from about 50 to about 1000 μm, and most preferably from about 100 to about 300 μm. Note that the diameter of the multiparticulates can be used to adjust the release rate of azithromycin from the multiparticulates. Generally, the smaller the diameter of the multiparticulates, the faster will be the azithromycin release rate from a particular multiparticulate formulation. This is because the overall surface area in contact with the dissolution medium increases as the diameter of the multiparticulates decreases. Thus, adjustments in the mean diameter of the multiparticulates can be used to adjust the azithromycin release profile.

The multiparticulates may be made by a melt-congeal process comprising the steps of (a) forming a molten mixture comprising azithromycin and a pharmaceutically acceptable carrier; (b) delivering the molten mixture of step (a) to an atomizing means to form droplets from the molten mixture; and (c) congealing the droplets from step (b) to form the multiparticulates.

When using thermal-based processes, such as the melt-congeal process, to make the multiparticulates of the present invention, the heat transfer to the azithromycin is minimized to prevent significant thermal degradation of the azithromycin during the process. It is also preferred that the carrier have a melting point that is less then the melting point of azithromycin. For example, azithromycin dihydrate has a melting point of 113° C. to 115° C. Thus, when azithromycin dihydrate is used in the multiparticulates of the present invention, it is preferred that the carrier have a melting point that is less than about 113° C. As used herein, the term "melting point of the carrier" or "$T_m$" means the temperature at which the carrier, when containing the drug and any optional excipients present in the multiparticulate, transitions from its crystalline to its liquid state. When the carrier is not crystalline, "melting point of the carrier" means the temperature at which the carrier becomes fluid in the sense that it will flow when subjected to one or more forces such as pressure, shear, and centrifugal force, in a manner similar to a crystalline material in the liquid state.

The azithromycin in the molten mixture may be dissolved in the molten mixture, may be a suspension of crystalline azithromycin distributed in the molten mixture, or any combination of such states or those states that are in between. Preferably, the molten mixture comprises a homogeneous suspension of crystalline azithromycin in the molten carrier where the fraction of azithromycin that melts or dissolves in the molten carrier is kept relatively low. Preferably less than about 30 wt % of the total azithromycin melts or dissolves in the molten carrier. It is preferred that the azithromycin be present as the crystalline dihydrate.

Thus, by "molten mixture" is meant that the mixture of azithromycin and carrier are heated sufficiently that the mixture becomes sufficiently fluid that the mixture may be formed into droplets or atomized. Atomization of the molten mixture may be carried out using any of the atomization methods described below. Generally, the mixture is molten in the sense that it will flow when subjected to one or more forces such as pressure, shear, and centrifugal force, such as that exerted by a centrifugal or spinning-disk atomizer. Thus, the azithromycin/carrier mixture may be considered "molten" when any portion of the carrier and azithromycin become fluid such that the mixture, as a whole, is sufficiently fluid that it may be atomized. Generally, a mixture is sufficiently fluid for atomization when the viscosity of the molten mixture is less than about 20,000 cp, preferably less than about 15,000 cp, more preferably less than about 10,000 cp. Often, the mixture becomes molten when the mixture is heated above the melting point of one or more of the carrier components, in cases where the carrier is sufficiently crystalline to have a relatively sharp melting point; or, when the carrier components are amorphous, above the softening point of one or more of the carrier components. Thus, the molten mixture is often a suspension of solid particles in a fluid matrix. In one preferred embodiment, the molten mixture comprises a mixture of substantially crystalline azithromycin particles suspended in a carrier that is substantially fluid. In such cases, a portion of the azithromycin may be dissolved in the fluid carrier and a portion of the carrier may remain solid.

Although the term "melt" refers specifically to the transition of a crystalline material from its crystalline to its liquid state, which occurs at its melting point, and the term "molten" refers to such a crystalline material in its liquid state, as used herein, the terms are used more broadly, referring in the case of "melt" to the heating of any material or mixture of materials sufficiently that it becomes fluid in the sense that it may be pumped or atomized in a manner similar to a crystalline material in the liquid state. Likewise "molten" refers to any material or mixture of materials that is in such a fluid state.

Virtually any process can be used to form the molten mixture. One method involves melting the carrier in a tank, adding the azithromycin to the molten carrier, and then mixing the mixture to ensure the azithromycin is uniformly distributed therein. Alternatively, both the azithromycin and carrier may be added to the tank and the mixture heated and mixed to form the molten mixture. When the carrier comprises more than one material, the molten mixture may be prepared using two tanks, melting a first carrier in one tank and a second in another. The azithromycin is added to one of these tanks and mixed as described above. In another method, a continuously stirred tank system may be used, wherein the azithromycin and carrier are continuously added to a heated tank equipped with means for continuous mixing, while the molten mixture is continuously removed from the tank.

The molten mixture may also be formed using a continuous mill, such as a Dyno® Mill. The azithromycin and carrier are typically fed to the continuous mill in solid form, entering a grinding chamber containing grinding media, such as beads 0.25 to 5 mm in diameter. The grinding chamber typically is jacketed so heating or cooling fluid may be circulated around the chamber to control its temperature. The molten mixture is formed in the grinding chamber, and exits the chamber through a separator to remove the grinding media.

An especially preferred method of forming the molten mixture is by an extruder. By "extruder" is meant a device or collection of devices that creates a molten extrudate by heat and/or shear forces and/or produces a uniformly mixed extrudate from a solid and/or liquid (e.g., molten) feed. Such devices include, but are not limited to single-screw extruders; twin-screw extruders, including co-rotating, counter-rotating, intermeshing, and non-intermeshing extruders; multiple screw extruders; ram extruders, consisting of a heated cylinder and a piston for extruding the molten feed; gear-pump extruders, consisting of a heated gear pump, generally counter-rotating, that simultaneously heats and pumps the molten feed; and conveyer extruders. Conveyer extruders comprise a conveyer means for transporting solid and/or powdered feeds, such, such as a screw conveyer or pneumatic conveyer, and a pump. At least a portion of the conveyer means is heated to a sufficiently high temperature to produce the molten mixture. The molten mixture may optionally be directed to an accumulation tank, before being directed to a pump, which directs the molten mixture to an atomizer. Optionally, an in-line mixer may be used before or after the pump to ensure the molten mixture is substantially homogeneous. In each of these extruders the molten mixture is mixed to form a uniformly mixed extrudate. Such mixing may be accomplished by various mechanical and processing means, including mixing elements, kneading elements, and shear mixing by backflow. Thus, in such devices, the composition is fed to the extruder, which produces a molten mixture that can be directed to the atomizer.

Once the molten mixture has been formed, it is delivered to an atomizer that breaks the molten mixture into small droplets. Virtually any method can be used to deliver the molten mixture to the atomizer, including the use of pumps and various types of pneumatic devices such as pressurized vessels or piston pots. When an extruder is used to form the molten mixture, the extruder itself can be used to deliver the molten mixture to the atomizer. Typically, the molten mixture is maintained at an elevated temperature while delivering the mixture to the atomizer to prevent solidification of the mixture and to keep the molten mixture flowing.

Generally, atomization occurs in one of several ways, including (1) by "pressure" or single-fluid nozzles; (2) by two-fluid nozzles; (3) by centrifugal or spinning-disk atomizers; (4) by ultrasonic nozzles; and (5) by mechanical vibrating nozzles. Detailed descriptions of atomization processes, including how to use spinning disk atomizers to obtain specific particle sizes, can be found in Lefebvre, *Atomization and Sprays* (1989) or in *Perry's Chemical Engineers' Handbook* (7th Ed. 1997).

Once the molten mixture has been atomized, the droplets are congealed, typically by contact with a gas or liquid at a temperature below the solidification temperature of the droplets. Typically, it is desirable that the droplets are congealed in less than about 60 seconds, preferably in less than about 10 seconds, more preferably in less than about 1 second. Often, congealing at ambient temperature results in sufficiently rapid solidification of the droplets to avoid excessive azithromycin ester formation. However, the congealing step often occurs in an enclosed space to simplify collection of the multiparticulates. In such cases, the temperature of the congealing medium (either gas or liquid) will increase over time as the droplets are introduced into the enclosed space, leading to the possible formation of azithromycin esters. Thus, a cooling gas or liquid is often circulated through the enclosed space to maintain a constant congealing temperature. When the carrier used is highly reactive with azithromycin and the time the azithromycin is exposed to the molten carrier must be limited, the cooling gas or liquid can be cooled to below ambient temperature to promote rapid congealing, thus keeping the formation of azithromycin esters to acceptable levels.

Suitable thermal-based processes are disclosed in detail in U.S. patent application Ser. No. 60/527,244, titled "Improved Azithromycin Multiparticulate Dosage Forms by Melt-Congeal Processes", and U.S. patent application Ser. No. 60/527,615, titled "Extrusion Process for Forming Chemically Stable Multiparticulates", filed concurrently herewith.

The multiparticulates may also be made by a liquid-based process comprising the steps of (a) forming a mixture comprising azithromycin, a pharmaceutically acceptable carrier, and a liquid; (b) forming particles from the mixture of step (a); and (c) removing a substantial portion of the liquid from the particles of step (b) to form multiparticulates. Preferably, step (b) is a method selected from (i) atomization of the mixture, (ii) coating seed cores with the mixture, (iii) wet-granulating the mixture, and (iv) extruding the mixture into a solid mass followed by spheronizing or milling the mass.

Preferably, the liquid has a boiling point of less than about 150° C. Examples of liquids suitable for formation of multiparticulates using liquid-based processes include water; alcohols, such as methanol, ethanol, various isomers of propanol and various isomers of butanol; ketones, such as acetone, methyl ethyl ketone and methyl isobutyl ketone; hydrocarbons, such as pentane, hexane, heptane, cyclohexane, methylcyclohexane, octane and mineral oil; ethers, such as methyl tert-butyl ether, ethyl ether and ethylene glycol monoethyl ether; chlorocarbons, such as chloroform, methylene dichloride and ethylene dichloride; tetrahydrofuran; dimethylsulfoxide; N-methylpyrrolidinone; N,N-dimethylacetamide; acetonitrile; and mixtures thereof.

In one embodiment, the particles are formed by atomization of the mixture using an appropriate nozzle to form small droplets of the mixture, which are sprayed into a drying chamber where there is a strong driving force for evaporation of the liquid, to produce solid, generally spherical particles. The strong driving force for evaporation of the liquid is generally provided by maintaining the partial pressure of liquid in the drying chamber well below the vapor pressure of the liquid at the temperature of the particles. This is accomplished by (1) maintaining the pressure in the drying chamber at a partial vacuum (e.g., 0.01 to 0.5 atm); or (2) mixing the droplets with a warm drying gas; or (3) both (1) and (2). Spray-drying processes and spray-drying equipment are described generally in *Perry's Chemical Engineers' Handbook*, pages 20–54 to 20–57 (6th Ed. 1984).

In another embodiment, the particles are formed by coating the liquid mixture onto seed cores. The seed cores can be made from any suitable material such as starch, microcrystalline cellulose, sugar or wax, by any known method, such as melt- or spray-congealing, extrusion/spheronization, granulation, spray-drying and the like.

The liquid mixture can be sprayed onto such seed cores using coating equipment known in the pharmaceutical arts, such as pan coaters (e.g., Hi-Coater available from Freund Corp. of Tokyo, Japan, Accela-Cota available from Manesty of Liverpool, U.K.), fluidized bed coaters (e.g., Würster coaters or top-spray coaters, available from Glatt Air Technologies, Inc. of Ramsey, N.J. and from Niro Pharma Systems of Bubendorf, Switzerland) and rotary granulators (e.g., CF-Granulator, available from Freund Corp).

In another embodiment, the liquid mixture may be wet-granulated to form the particles. Granulation is a process by which relatively small particles are built up into larger granular particles, often with the aid of a carrier, also known as a binder in the pharmaceutical arts. In wet-granulation, a liquid is used to increase the intermolecular forces between particles, leading to an enhancement in granular integrity, referred to as the "strength" of the granule. Often, the strength of the granule is determined by the amount of liquid that is present in the interstitial spaces between the particles during the granulation process. This being the case, it is important that the liquid wet the particles, ideally with a contact angle of zero. Since a large percentage of the particles being granulated are very hydrophilic azithromycin crystals, the liquid needs to be fairly hydrophilic to meet this criterion. Thus, effective wet-granulation liquids tend also to be hydrophilic. Examples of liquids found to be effective wet-granulation liquids include water, ethanol, isopropyl alcohol and acetone. Preferably, the wet-granulation liquid is water at pH 7 or higher.

Several types of wet-granulation processes can be used to form azithromycin-containing multiparticulates. Examples include fluidized bed granulation, rotary granulation and high-shear mixers. In fluidized bed granulation, air is used to agitate or "fluidize" particles of azithromycin and/or carrier in a fluidizing chamber. The liquid is then sprayed into this fluidized bed, forming the granules. In rotary granulation, horizontal discs rotate at high speed, forming a rotating "rope" of azithromycin and/or carrier particles at the walls of the granulation vessel. The liquid is sprayed into this rope, forming the granules. High-shear mixers contain an agitator or impeller to mix the particles of azithromycin and/or carrier. The liquid is sprayed into the moving bed of particles, forming granules. In these processes, all or a portion of the carrier can be dissolved into the liquid prior to spraying the liquid onto the particles. Thus, in these processes, the steps of forming the liquid mixture and forming particles from the liquid mixture occur simultaneously.

In another embodiment, the particles are formed by extruding the liquid mixture into a solid mass followed by spheronizing or milling the mass. In this process, the liquid mixture, which is in the form of a paste-like plastic suspension, is extruded through a perforated plate or die to form a solid mass, often in the form of elongated, solid rods. This solid mass is then milled to form the multiparticulates. In one embodiment, the solid mass is placed, with or without an intervening drying step, onto a rotating disk that has protrusions that break the material into multiparticulate spheres, spheroids, or rounded rods. The so-formed multiparticulates are then dried to remove any remaining liquid. This process is sometimes referred to in the pharmaceutical arts as an extrusion/spheronization process.

Once the particles are formed, a portion of the liquid is removed, typically in a drying step, thus forming the multiparticulates. Preferably, at least 80% of the liquid is removed from the particles, more preferably at least 90%, and most preferably at least 95% of the liquid is removed from the particle during the drying step.

Suitable liquid-based processes are disclosed more fully in U.S. patent application Ser. No. 11/004,453, titled "Improved Azithromycin Multiparticulate Dosage Forms by Liquid-Based Processes", filed concurrently herewith.

The multiparticulates may also be made by a granulation process comprising the steps of (a) forming a solid mixture comprising azithromycin and a pharmaceutically acceptable carrier; and (b) granulating the solid mixture to form multiparticulates. Examples of such granulation processes include dry granulation and melt granulation, both well known in the art. See *Remington's Pharmaceutical Sciences* (18th Ed. 1990).

An example of a dry granulation process is roller compaction. In roller compaction processes, the solid mixture is compressed between rollers. The rollers can be designed such that the resulting compressed material is in the form of small beads or pellets of the desired diameter. Alternatively, the compressed material is in the form of a ribbon that may be milled to for multiparticulates using methods well known in the art. See, for example, *Remington's Pharmaceutical Sciences* (18th Ed. 1990).

In melt granulation processes, the solid mixture is fed to a granulator that has the capability of heating or melting the carrier. Equipment suitable for use in this process includes high-shear granulators and single or multiple screw extruders, such as those described above for melt-congeal processes. In melt granulation processes, the solid mixture is placed into the granulator and heated until the solid mixture agglomerates. The solid mixture is then kneaded or mixed until the desired particle size is attained. The so-formed granules are then cooled, removed from the granulator and sieved to the desired size fraction, thus forming the multiparticulates.

While the azithromycin in the multiparticulates can be amorphous or crystalline, it is preferred that a substantial portion of the azithromycin is crystalline, preferably the crystalline dihydrate. By "substantial portion" is meant that at least 80% of the azithromycin is crystalline. The crystalline form is preferred because it tends to result in multiparticulates with improved chemical and physical stability. The crystallinity of azithromycin in the multiparticulates is determined using Powder X-Ray Diffraction (PXRD) analysis. In an exemplary procedure, PXRD analysis may be performed on a Bruker AXS D8 Advance diffractometer. In this analysis, samples of about 500 mg are packed in Lucite sample cups and the sample surface smoothed using a glass microscope slide to provide a consistently smooth sample surface that is level with the top of the sample cup. Samples are spun in the $\phi$ plane at a rate of 30 rpm to minimize crystal orientation effects. The X-ray source (S/B Kcu$_\alpha$, $\lambda$=1.54 Å) is operated at a voltage of 45 kV and a current of 40 mA. Data for each sample are collected over a period of from about 20 to about 60 minutes in continuous detector scan mode at a scan speed of about 12 seconds/step and a step size of 0.02°/step. Diffractograms are collected over the 2θ range of 10° to 16°.

The crystallinity of the test sample is determined by comparison with calibration standards as follows. The calibration standards consist of physical mixtures of 20 wt %/80 wt % azithromycin/carrier, and 80 wt %/20 wt % azithromycin/carrier. Each physical mixture is blended together 15 minutes on a Turbula mixer. Using the instrument software, the area under the diffractogram curve is integrated over the 2θ range of 10° to 16° using a linear baseline. This integration range includes as many azithromycin-specific peaks as possible while excluding carrier-related peaks. In addition, the large azithromycin-specific peak at approximately 10° 2θ is omitted due to the large scan-to-scan variability in its integrated area. A linear calibration curve of percent crystalline azithromycin versus the area under the diffractogram curve is generated from the calibration standards. The crystallinity of the test sample is then determined using these calibration results and the area under the curve for the test sample. Results are reported as a mean percent azithromycin crystallinity (by crystal mass).

One key to maintaining the crystalline form of azithromycin during formation of multiparticulates via thermal-based and liquid-based processes is to maintain a high activity of water and any solvate solvents in the carrier, atmosphere or gas with which the composition comes in contact. The activity of water or solvent should be equivalent to or greater than that in the crystalline state. This will ensure that the water or solvent present in the crystal form of azithromycin remains at equilibrium with the atmosphere, thus preventing a loss of hydrated water or solvated solvent. For example, if the process for forming the multiparticulates requires that crystalline azithromycin, the crystalline dihydrate, for instance, be exposed to high temperatures (e.g., during a melt- or spray-congeal process), the atmosphere near the azithromycin should be maintained at high humidity to limit the loss of the hydrated water from the azithromycin crystals, and thus a change in the crystalline form of the azithromycin.

The humidity level required is that equivalent to or greater than the activity of water in the crystalline state. This can be determined experimentally, for example, using a dynamic vapor sorption apparatus. In this test, a sample of the crystalline azithromycin is placed in a chamber and equilibrated at a constant temperature and relative humidity. The weight of the sample is then recorded. The weight of the sample is then monitored as the relative humidity of the atmosphere in the chamber is decreased. When the relative humidity in the chamber decreases to below the level equivalent to the activity of water in the crystalline state, the sample will begin to loose weight as waters of hydration are lost. Thus, to maintain the crystalline state of the azithromycin, the humidity level should be maintained at or above the relative humidity at which the azithromycin begins to lose weight. A similar test can be used to determine the appropriate amount of solvent vapor required to maintain a crystalline solvate form of azithromycin.

When crystalline azithromycin, such as the dihydrate form, is added to a molten carrier, a small amount of water, on the order of 30 to 100 wt % of the solubility of water in the molten carrier at the process temperature can be added to the carrier to ensure there is sufficient water to prevent loss of the azithromycin dihydrate crystalline form.

Likewise, if a liquid-based process is used to form the composition, the liquid should contain sufficient water (e.g., 30 to 100 wt % the solubility of water in the liquid) to prevent a loss of the waters from hydrated crystalline azithromycin. In addition, the atmosphere near the azithromycin during any drying steps to remove the liquid should be humidified sufficiently to prevent the loss of water and thereby maintain the crystalline dihydrate form. Generally, the higher the processing temperature, the higher the required concentration of water vapor or solvent in the carrier, atmosphere, or gas to which the azithromycin is exposed to maintain the hydrated or solvated form of the azithromycin.

Processes to maintain the crystalline form of azithromycin while forming multiparticulates are disclosed more fully in U.S. patent application Ser. No. 11/003,659, filed concurrently herewith.

The multiparticulates of the present invention may be post-treated to improve the drug crystallinity and/or the stability of the multiparticulate. In one embodiment, the multiparticulates comprise azithromycin and a carrier, wherein the carrier, when in the multiparticulate, and containing the azithromycin and optional excipients has a melting point of $T_m$ in 0° C.; the multiparticulates are treated after formation by at least one of(i) heating the multiparticulates to a temperature of at least 35° C. but less than ($T_m$° C.–10° C.), and (ii) exposing the multiparticulates to a mobility-enhancing agent. Such a post-treatment step results in an increase in drug crystallinity in the multiparticulates, and typically an improvement in at least one of the chemical stability, physical stability, and dissolution stability of the multiparticulates. Post-treatment processes are disclosed more fully in U.S. patent application Ser. No. 11/003,664, filed concurrently herewith.

Preferably, wherein the azithromycin dosage form comprises azithromycin multiparticulates, which comprise about 45 to about 55 wt % azithromycin, about 43 to about 50 wt % glyceryl behenate and about 2 to about 5 wt % poloxamer, and an alkalizing agent comprising about 300 to about 400 mg TSP, the azithromycin multiparticulates are post-treated by maintaining them at a temperature of about 40° C. at a relative humidity of about 75%, or sealed with water in a container maintained at 40° C., for 2 days or more. It is more preferred that this dosage form further comprises about 200 to about 300 mg magnesium hydroxide.

More preferably, wherein the azithromycin dosage form comprises azithromycin multiparticulates, which comprise about 50 wt % azithromycin dihydrate, about 46 to about 48 wt % Compritol® 888 ATO, and about 2 to about 4 wt % Lutrol® F127 NF; and an alkalizing agent comprising about 300 to about 400 mg TSP, the azithromycin multiparticulates are post-treated by maintaining them at a temperature of about 40° C. at a relative humidity of about 75%, or sealed with water in a container maintained at 40° C., for about 5 days to about 3 weeks. It is more preferred that this dosage form further comprises about 200 to about 300 mg magnesium hydroxide.

Most preferably, wherein the azithromycin dosage form comprises azithromycin the multiparticulates, which comprises about 50 wt % azithromycin dihydrate, about 47 wt % Compritol® 888 ATO and about 3 wt % Lutrol® F127 NF, the azithromycin multiparticulates are post-treated by maintaining them at a temperature of about 40° C. at a relative humidity of about 75%, or sealed with water in a container maintained at 40° C., for about 10 days or more.

Preferably, the concentration of azithromycin esters in the multiparticulates is less than about 1 wt %, based on the total amount of azithromycin present in the multiparticulate, more preferably less than about 0.5 wt %, more preferably less than about 0.2 wt %, and most preferably less than about 0.1 wt %.

Azithromycin esters may be formed during the multiparticulate-forming process, during other processing steps required for manufacture of the finished dosage form, or during storage following manufacture but prior to dosing. Since the azithromycin dosage forms may be stored for up to two years or even longer prior to dosing, it is preferred that the amount of azithromycin esters in the stored dosage form not exceed the above values prior to dosing.

Processes for reducing ester formation are described in more detail in commonly assigned U.S. patent application Ser. Nos. 11/003,856, 11/003,853, and 11/004,453, filed concurrently herewith.

The invention also provides a method of treating a disease or condition amenable to treatment with azithromycin, comprising administering to a mammal, preferably a human, in need of such treatment a therapeutically effective amount of azithromycin and an effective amount of an alkalizing agent. It is also preferred that the azithromycin is in multiparticulate form.

The term "effective amount of azithromycin" means the amount of azithromycin which, when administered, according to the present invention, prevents the onset of, alleviates the symptoms of, stops the progression of, or eliminates a bacterial or protozoal infection in a mammal.

In a preferred embodiment, the pharmaceutical dosage forms of the present invention are be used to treat bacterial or protozoal infection(s). As relates to bacterial or protozoal infections, the term "treat", means to treat or prevent bacterial or protozoal infection(s), including curing, reducing the symptoms of or slowing the progress of said infection(s).

As used herein, unless otherwise indicated, the term "bacterial or protozoal infection(s)" includes bacterial infections and protozoal infections that occur in mammals as well as disorders related to bacterial infections and protozoal infections that may be treated or prevented by administering antibiotics such as the compound of the present invention. Such bacterial infections and protozoal infections and disorders related to such infections include, but are not limited to, the following: pneumonia, otitis media, sinusitis, bronchitis, tonsillitis, and mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, and glomerulonephritis related to infection by *Streptococcus pyogenes,* Groups C and G streptococci, *Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus,* etc.), *Streptococcus pyogenes, Streptococcus agalactiae,* Streptococcal Groups C–F (minute-colony streptococci), *viridans streptococci, Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum,* or *Neisseria gonorroeae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp.; odontogenic infection related to infection by *viridans streptococci*; persistent cough related to infection by *Bordetella pertussis*; gas gangrene related to infection by *Clostridium perfringens* or *Bacteroides* spp.; and atherosclerosis related to infection by *Helicobacter pylori* or *Chlamydia pneumoniae*. Bacterial infections and protozoal infections and disorders related to such infections that may be treated or prevented in animals include, but are not limited to, the following: bovine respiratory disease related to infection by *P. haem., P. multocida, Mycoplasma bovis*, or *Bordetella* spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae, Klebsiella* spp., *Corynebacterium*, or *Enterococcus* spp.; swine respiratory disease related to infection by *A. pleuro., P. multocida*, or *Mycoplasma* spp.; swine enteric disease related to infection by *E. coli, Lawsonia intracellularis, Salmonella*, or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. *neosporium*); urinary tract infection in dogs and cats related to infection by *E. coli*; skin and soft tissue infections in dogs and cats related to infection by *Staph. epidermidis, Staph. intermedius*, coagulase neg. *Staph.* or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas*, or *Prevotella*. Other conditions that may be treated by the compounds and preparations of the present invention include malaria and atherosclerosis. Other bacterial infections and protozoal infections and disorders related to such infections that may be treated or prevented in accord with the method and compositions of the present invention are referred to in J. P. Sanford et al., "The Sanford Guide To Antimicrobial Therapy," 26th Edition, (Antimicrobial Therapy, Inc., 1996).

The amount of azithromycin which is administered will necessarily be varied according to principles well known in the art, taking into account factors such as the severity of the disease or condition being treated and the size and age of the patient. In general, the drug is to be administered so that an effective dose is received, with the effective dose being determined from safe and efficacious ranges of administration already known for azithromycin.

For adult humans, and for pediatric humans weighing more than 30 kg, the amount of azithromycin administered in a dose is typically between about 250 mgA and about 7 gA. Preferably, for adult humans, and for pediatric humans above 30 kg in weight, the dose form contains between about 1.5 to about 4 gA, more preferably about 1.5 to about 3 gA, and most preferably about 1.8 to about 2.2 gA. For pediatric humans weighing 30 kg, or less, the azithromycin dose is typically scaled, according to the weight of the patient, and contains about 30 to about 90 mgA/kg of patient body weight, preferably about 45 to about 75 mgA/kg, and more preferably about 60 mgA/kg.

The present invention is particularly useful for administering relatively large amounts of azithromycin to a patient, with reduced GI side effects, in a single-dose therapy wherein the total dose administered in the therapy comprises about 1.5 gA to about 4.0 gA of azithromycin. Even more preferably, this single dose comprises about 1.5 gA to about 3.0 gA of azithromycin and most preferably 1.8 to 2.2 gA azithromycin.

For animal/veterinary applications, the amount can, of course, be adjusted to be outside these limits depending, for example, on the size of the animal subject being treated.

In the method of the present invention, the azithromycin may be administered using a single-dose therapy or in multiple-dose therapy (e.g., administering more than one dose in a single day or administering one or more doses over a course of 2–5 days or more). A daily dosage can be administered from 1 to 4 times daily in equal doses. Preferably, the azithromycin is administered one dose per day.

Most preferably, in the method of the present invention, the azithromycin is administered using a single dose, single-day therapy.

"Single dose" as used herein, means administering only one dose of azithromycin in the full course of therapy.

Exemplification

The present invention will be further illustrated by means of the following examples. It is to be understood, however, that the invention is not meant to be limited to the details described therein.

In the examples that follow, the following definitions and tests have been employed:

Specification of a quantity in percent (%) means percent by weight based on total weight, unless otherwise indicated.

Lutrol® F127 NF (hereinafter referred to as "Lutrol®") and Pluronic® F127 (hereinafter referred to as "Pluronic®"), which are also known as Poloxamer 407 NF, are polyoxypropylene-polyoxyethylene block copolymers having a molecular weight, calculated on the OH value, of 9,840 to 14,600 g/mol and having a general structure of

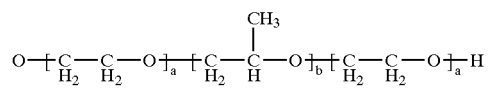

wherein a is about 101 and b is about 56, obtained from BASF Corporation, Mount Olive, N.J. Lutrol® is the pharmaceutical equivalent of Pluronic®.

Compritol® 888 ATO (hereinafter referred to as "Compritol®"), which is composed of a mixture of glyceryl mono-, di- and tribehenates, the diester fraction being predominant, is synthesized by esterification of glycerol by behenic acid (C22 fatty acid) and then atomized by spray-cooling, was obtained from GATTEFOSSÉ Corporation, Saint Priest, Cedex, France.

"gA" is an abbreviation for "grams of active azithromycin". For example, "2 gA" means 2 grams of active azithromycin.

EXAMPLE 1

Effect of Various Alkalizing Agents on Stomach pH

A clinical study was conducted to monitor the pH of the stomach (using a pH probe) after dosing six different formulations containing alkalizing agents. Prior to performing the clinical study, a titration study was conducted with the alkalizing agent formulation to determine the pH change resulting from adding 0.1N HCl (pH 1.2) to the alkalizing agent.

The formulations tested included the following alkalizing agents:

Formulation 1–176 mg anhydrous TSP
Formulation 2–352 mg anhydrous TSP
Formulation 3–352 mg anhydrous TSP and 500 mg calcium carbonate Formulation 4—352 mg anhydrous TSP and 250 mg magnesium hydroxide Formulation 5—352 mg anhydrous TSP and 500 mg Tromethamine (TRIS)

Formulation 6—352 mg anhydrous TSP and 1000 mg Tromethamine (TRIS)

Further, each formulation was prepared by blending the specified alkalizing agent with 19.36 g sucrose, 0.067 g hydroxypropyl cellulose, 0.067 g xanthan gum, 0.2 g colloidal silicon dioxide, 0.14 g artificial cherry flavor, 0.23 g artificial banana flavor, and 0.4 g titanium dioxide.

Step A—In Vitro Titration of Alkalizing Agents

In vitro titration curves for each of the six formulations were developed. A volume of 60 mL water was used to constitute suspensions of each formulation and of the placebo. In vitro titration curves, for each suspension, were then determined by titrating the suspension with 0.2 mL to 5 mL increments of 0.1N HCl where the size of the subsequent increment depended upon the pH change associated with the prior increment. Titration curves for suspensions containing magnesium hydroxide or calcium carbonate were allowed to equilibrate for approximately 5 minutes after each acid addition prior to reading pH values. The in vitro test results for each of the formulations are provided in FIG. 1.

The data in FIG. 1 is used in the method to estimate the change in stomach pH with time after ingestion of an alkalizing agent. To calculate this, one must assume the amount of acid present in the stomach and also the rate of acid produced. From the literature (C. Lentner. Basle, CIBA-GEIGY, Units of measurement, Body Fluids, Composition of the Body, Nutrition, Geigy Scientific Tables (1981) 1:123–133; Yamada, Tadataka (ed.), "Textbook of Gastroenterology", Volume 1, Lippincott Williams & Wilkens, 1999, pp. 284–285), the basal fasted stomach acid volume content is 40 mL of 0.04M HCl, or 0.96 mEq H+ or 9.6 mL of 0.1N HCl (0.1 mmol/mL). The basal acid secretion rate is 3 mEq/hr (or 3/60=0.05 mEq/min). For H+, the number of milliequivalents (mEq) is the same as the number of mmoles. The calculation procedure further assumes that equilibrium conditions apply (i.e., good mixing) and that there is no stomach emptying of the formulation as well as gastric acid. It will be recognized by those skilled in the art of acid-base equilibria that under the assumptions discussed above, theoretically estimating the change in stomach pH with time after ingestion of an alkalizing agent is mathematically identical to estimating the pH of the alkalizing agent formulation with time after (1) adding the entire basal amount of acid (0.96 mmol) to the formulation at time zero, and (2) simultaneously adding acid at the rate of 0.05 mmol/min to the formulation at time greater than 0. At any given time t, the volume of 0.1N HCl, V, that corresponds to these conditions is calculated as follows:

$$V=0.96 \text{ mmol}/(0.1 \text{ mmol/mL})+(0.05 \text{ mmol/min})/(0.1 \text{ mmol/mL}) \times t(\text{min})$$

[Note: 0.1 mmol/mL is the definition of 0.1N HCl]

Therefore, $$t=(V-9.6)/0.5,$$

where t is time in minutes and V is the volume of 0.1 N HCl in FIG. 1.

Figure 2:
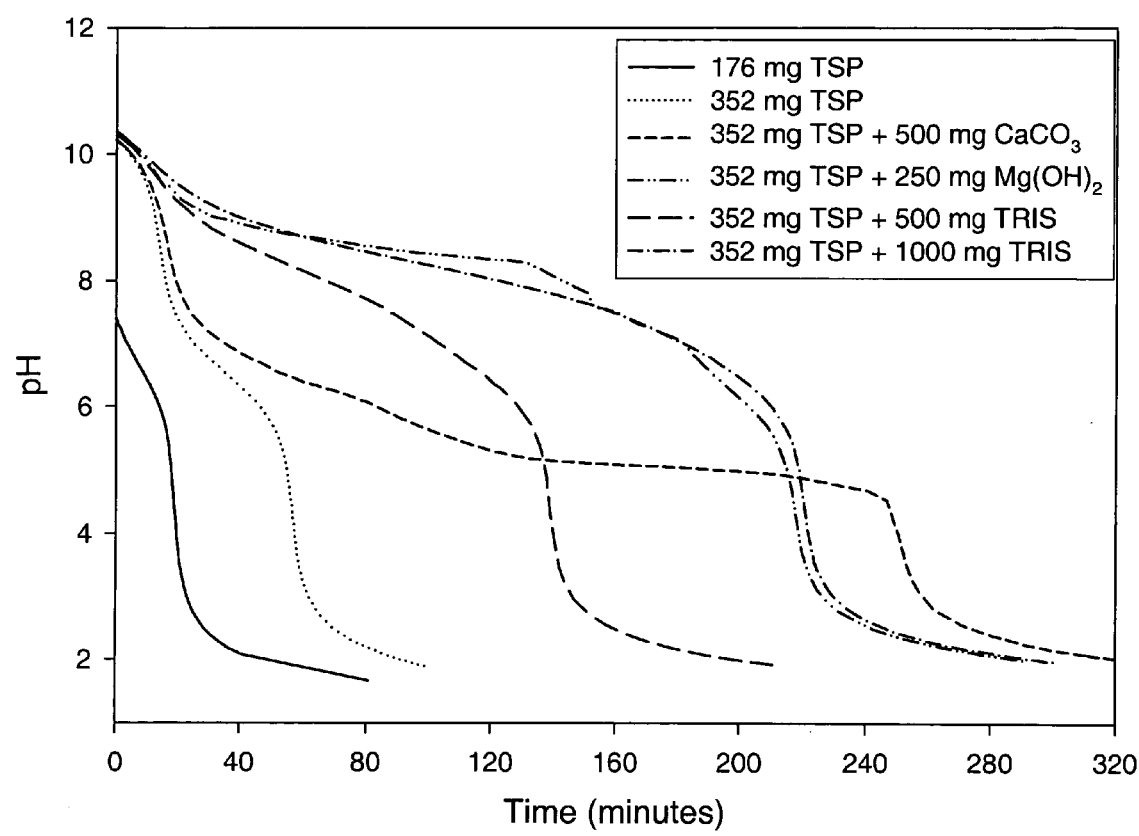
FIG. 2, which is further discussed in Examples 1 and 8, shows the calculated pH of different alkalizing agents when titrated with 0.1N HCl over time.

For various alkalizing agent formulations, the pH versus time plots (theoretically calculated) are shown in FIG. 2.

Step B—Clinical Study

The study was an open, randomized, placebo-controlled study on gastric pH in healthy adult volunteers, specifically, eighteen (18) healthy adult volunteers (6 subjects per group) between 18 to 55 years of age and within 15% to 30% of the recommended weight range based on gender, height and body frame.

Subjects were assigned to three different groups. Each group received two test formulations and a placebo treatment in a 3-way cross over design:

Group 1: Formulation 1, Formulation 2 and placebo

Group 2: Formulation 3, Formulation 4 and placebo

Group 3: Formulation 5, Formulation 6 and placebo

Subjects were randomized to treatment sequences within each group. The test formulation was administered as single dose oral solution. Water was used as a placebo. Each subject received only one treatment (formulation) per day. There was a minimum of a 1-day wash out period between treatment days.

Prior to dosing, the following procedures were performed: Each subject was intubated with the Synectics Digitrapper pH probe (Synectics Medical Ltd, Middlesex, UK) approximately 30 minutes prior to the administration of the alkalizing agent formulation or the placebo to obtain a baseline pH. Continuous pH recording was done from 30 minutes prior to dose administration while in a sitting position. If a baseline pH of <2.0 was not demonstrated for a subject, that subject would have been excluded from the study. However, no subjects were excluded.

The test dose of a Formulation (1, 2, 3, 4, 5 or 6) or placebo, depending upon the allocated group and treatment sequence, was then administered orally. The dose was swallowed easily around the Digitrapper. In order to standardize conditions, all subjects were required to refrain from lying down, and eating and drinking beverages (including water) during the first 2 hours after dosing. Continuous pH recording was done until 2 hours post dose in a sitting position.

Given some subject-to-subject variability for all formulations, the following conclusions were made.

TRIS containing formulations, in general, exhibited the longest duration of pH rise of all formulations.

Response by subject to calcium carbonate containing formulation was equal or greater than that of magnesium hydroxide containing formulation. Except for Formulation 1, all other formulations, on average, raised the pH to 6, or above, for at least 20 minutes.

EXAMPLE 2

Comparison of In Vitro Release Rates From Dosage Forms with Different Amounts of the Same Alkalizing Agent The in vitro release rates of azithromycin were determined for various azithromycin sustained release dosage forms, which each contained 2 gA of the same azithromycin multiparticulate (MP1) and varying amounts of TSP as an alkalizing agent, as compared to an azithromycin dosage form containing MP1 multiparticulates and no TSP, and to an azithromycin immediate release dosage form which did contain TSP. The sustained release dosage forms were prepared as described in Step A, below, while the in vitro release rate study, and its results, are described in the following Step B.

Step A—Preparation of Azithromycin Sustained Release Dosage Forms

Five azithromycin sustained release dosage forms (hereinafter "SR1", "SR2", "SR3", "SR4", "SR5") were prepared by mixing 2000 mgA of azithromycin multiparticulates MP1, prepared as described below, with one of six excipient blends, as described below in this example:

SR1 included 38.7 g sucrose and 50 mg TSP,
SR2 included 38.7 g sucrose and 100 mg TSP,
SR3 included 38.7 g sucrose and 264 mg TSP,
SR4 included 38.7 g sucrose and 356 mg TSP, and
SR5 included 38.7 g sucrose and 500 mg TSP.

In addition, a Multiparticulate Control dosage form was prepared by mixing 2000 mgA of azithromycin multiparticulates, described in this example, and 38.7 g sucrose.

Azithromycin Multiparticulates "MP1"

Azithromycin multiparticulates MP1 were made which comprised 50 wt % azithromycin dihydrate, 46 wt % Compritol®, and 4 wt % "Lutrol®". Specifically, azithromycin dihydrate (5000 g), Compritol® (4600 g) and Lutrol® (400 g) were blended in a twinshell blender (Blend Master C419145 purchased from Patterson Kelly, East Stroudsberg, Pa.) for 20 minutes. This blend was then de-lumped using a FitzMill® Comminutor L1A mill (The Fitzpatrick Company, Elmhurst, Ill.) at 3000 rpm, knives forward using a 0.065-inch screen. The mixture was blended again in a twinshell blender for 20 minutes, forming a preblend feed. The preblend feed was delivered to a B&P 19-mm twin-screw extruder (MP19-TC with a 25 L/D ratio purchased from B & P Process Equipment and Systems, LLC, Saginaw, Mich.) at a rate of 120 g/min, to form the molten mixture at a temperature of about 90° C. No water was added to the extruder. The extruder produced a molten mixture consisting of a suspension of the azithromycin dihydrate in the Compritol®/Lutrol®. The molten mixture was then fed into the center of spinning-disk atomizer to form azithromycin multiparticulates.

The spinning disk atomizer, which was custom made, consists of a bowel-shaped stainless steel disk of 10.1 cm (4 inches) in diameter. The surface of the disk is heated with a thin film heater beneath the disk to about 90° C. That disk is mounted on a motor that drives the disk of up to approximately 10,000 RPM. The entire assembly is enclosed in a plastic bag of approximately 8 feet in diameter to allow congealing and to capture multiparticulates formed by the atomizer. Air is introduced from a port underneath the disk to provide cooling of the multiparticulates upon congealing and to inflate the bag to its extended size and shape.

A suitable commercial equivalent, to this spinning disk atomizer, is the FX1 100-mm rotary atomizer manufactured by Niro A/S (Soeborg, Denmark).

The surface of the spinning disk atomizer was maintained at 90° C., and the disk was rotated at 5500 rpm, while forming the azithromycin multiparticulates. The mean residence time of the azithromycin dihydrate in the extruder was about 60 seconds and the total time the azithromycin was in the molten suspension was less than about 3 minutes. The particles formed by the spinning-disk atomizer were congealed in ambient air and collected. The azithromycin multiparticulates, prepared by this method, had a diameter of about 200 µm.

The properties of the melt-congealed multiparticulates such as particle size can be controlled by the viscosity of the melt and processing conditions. Given the combination of the materials in the preferred embodiments in the present invention, the viscosity of the melt is unchanged as long as the temperature of the heating system is kept at 90° C. The size of azithromycin multiparticulates can be controlled by feed rate (the amount of molten materials charging onto the spinning disk atomizer) and the disk speed (4 inch diameter). For example, 200 µm particles can be formed by a combination of 1) feed rate at 8.4 kg/hr and disk speed at 5500 RPM or 2) feed rate at 20 kg/hr and disk speed at 5800 RPM, or 3) feed rate at 25 kg/hr and disk speed at 7100 RPM.

The azithromycin multiparticulates were subsequently post-treated by placing them in a shallow tray, at a depth of about 2 cm, and then placing the tray in a 40° C. oven, maintaining a 75% relative humidity, for 5 days.

Each azithromycin multiparticulate dosage form was prepared using 4.2 grams of azithromycin multiparticulates to provide an equivalent of 2 gA azithromycin.

Step B—In Vitro Azithromycin Release Rate Study

The in vitro rates of release of azithromycin, in 0.01 N HCl which simulates stomach fluid when in the fed state and was used instead of 0.1 N HCl to avoid acid degradation of the azithromycin, for the sustained release dosage forms (2 gA each) SR1, SR2, SR3, SR4, and SR5 which contained varying amounts of TSP as an alkalizing agent were determined. The in vitro release rate of the multiparticulate (2 gA), which contained no TSP, was also determined. Further, the in vitro release rate of the immediate release (IR) control, of two commercially sold single dose packets of azithromycin dihydrate for oral suspension (Zithromax®, Pfizer Inc., New York, N.Y.), was determined. Each single dose packet contained 1048 mg azithromycin dihydrate (1 gA), 88 mg TSP and other excipients.

The data in Table 1, shown below, demonstrate that the release rate of azithromycin, from these multiparticulates, is increasingly slowed when administered with increasing amounts of TSP.

This in vitro azithromycin release rate study, reflected in Table 1, was performed as follows. The sustained release dosage forms, each containing about 2 gA of azithromycin in multiparticulates, and multiparticulate control and the immediate release control, were placed into individual 125 mL bottles. Next, 60 mL of purified water was added, and the bottle was shaken for 30 seconds. The contents were added to a USP Type 2 dissoette flask equipped with Teflon-coated paddles rotating at 50 rpm. The flask contained a volume of 750 mL of 0.01 N HCl held at 37.0±0.5° C. The bottle was rinsed twice with 20 mL of the HCl from the flask, and the rinse was returned to the flask to make up a 750 mL final volume. A 3 mL sample of the fluid in the flask was then collected at 15, 30, 60, 120, and 180 minutes following addition of the multiparticulates to the flask. The samples were filtered using a 0.45-µm syringe filter prior to analyzing via High Performance Liquid Chromatography (Hewlett Packard 1100, Waters Symmetry $C_8$ column, 45:30:25 acetonitrile:methanol:25 mM $KH_2PO_4$ buffer at 1.0 mL/min, absorbance measured at 210 nm with a diode array spectrophotometer).

TABLE 1

| Formulation | Time (hr) | Total Azithromycin Released (mg) | Azithromycin Released (%) |
|---|---|---|---|
| SR1 | 0.08 | 350 | 17 |
| (50 mg TSP) | 0.25 | 760 | 38 |
| | 0.5 | 1130 | 57 |
| | 1 | 1440 | 72 |
| | 2 | 1610 | 81 |
| | 3 | 1680 | 84 |

TABLE 1-continued

| Formulation | Time (hr) | Total Azithromycin Released (mg) | Azithromycin Released (%) |
|---|---|---|---|
| SR2 | 0.08 | 340 | 17 |
| (100 mg TSP) | 0.25 | 740 | 37 |
| | 0.5 | 1020 | 51 |
| | 1 | 1260 | 63 |
| | 2 | 1420 | 71 |
| | 3 | 1520 | 76 |
| SR3 | 0.08 | 300 | 15 |
| (264 mg TSP) | 0.25 | 630 | 31 |
| | 0.5 | 880 | 44 |
| | 1 | 1160 | 58 |
| | 2 | 1400 | 70 |
| | 3 | 1480 | 74 |
| SR4 | 0.08 | 250 | 12 |
| (356 mg TSP) | 0.25 | 490 | 24 |
| | 0.5 | 710 | 35 |
| | 1 | 920 | 46 |
| | 2 | 1120 | 56 |
| | 3 | 1240 | 62 |
| SR5 | 0.08 | 160 | 8 |
| (500 mg TSP) | 0.25 | 340 | 17 |
| | 0.5 | 480 | 24 |
| | 1 | 640 | 32 |
| | 2 | 850 | 42 |
| | 3 | 1010 | 50 |
| Multiparticulate | 0.08 | 420 | 21 |
| Control | 0.25 | 860 | 43 |
| (No TSP) | 0.5 | 1160 | 58 |
| | 1 | 1460 | 73 |
| | 2 | 1660 | 83 |
| | 3 | 1720 | 86 |
| IR | 0.08 | 1050 | 79 |
| Control | 0.25 | 1180 | 88 |
| (176 mg TSP) | 0.5 | 1230 | 92 |
| | 1 | 1270 | 95 |
| | 2 | 1950 | 97 |
| | 3 | 1960 | 98 |

EXAMPLE 3

Comparison of In Vitro Release Rates in Dosage Forms Having Different Alkalizing Agents The in vitro release rates of azithromycin, in 0.01N HCl were determined for various azithromycin sustained release dosage forms, which each contained 2 gA of the azithromycin multiparticulates MP1 were prepared with one of three excipients blends, as described below:

"SR6" included 38.7 g sucrose and 100 mg of the weak base sodium carbonate,

"SR7" included 38.7 g sucrose and 50 mg magnesium hydroxide, and

"SR8" included 38.7 g sucrose and 1.0 g of Liquid Maalox(R) (smooth cherry, regular strength, from Novartis) which contains 37.1 mg aluminum hydroxide, 37.1 mg of magnesium hydroxide, and 3.7 mg simethicone.

The rates of release of azithromycin from these sustained release dosage forms were measured in vitro as described in Example 2. The results of these dissolution tests, which are provided in Table 2, below, showed that the addition of various alkalizing agents slowed the release of azithromycin from MP1 multiparticulates as compared to the release from these multiparticulates without an alkalizing agent shown in Table 1.

TABLE 2

| Formulation | Time (hr) | Azithromycin Released (mg) | Azithromycin Released (%) |
|---|---|---|---|
| SR6 | 0.08 | 130 | 10 |
| | 0.25 | 270 | 20 |
| | 0.5 | 430 | 32 |
| | 1 | 590 | 45 |
| | 2 | 1170 | 59 |
| | 3 | 1360 | 68 |
| SR7 | 0.08 | 210 | 16 |
| | 0.25 | 470 | 35 |
| | 0.5 | 670 | 50 |
| | 1 | 830 | 62 |
| | 2 | 1460 | 73 |
| | 3 | 1580 | 79 |
| SR8 | 0.08 | 220 | 17 |
| | 0.25 | 490 | 36 |
| | 0.5 | 650 | 49 |
| | 1 | 830 | 62 |
| | 2 | 1440 | 72 |
| | 3 | 1520 | 76 |

EXAMPLE 4

In Vitro Evaluation of the Effect of Alkalizing Agent Addition Upon Immediate Release Dosage Form Release Rates The comparative effect of the addition of an alkalizing agent upon in vitro release rates in 0.01N HCl was determined for the Zithromax® tablet azithromycin immediate release dosage from. Zithromax® tablets contain azithromycin dihydrate equivalent to 250 mgA azithromycin, dibasic calcium phosphate (138.84 mg), which is an alkalizing agent, and several other excipients.

The rates of release of azithromycin from Zithromax® tablets, with and without adding an additional alkalizing agent, specifically 176 mg TSP, were measuring in vitro as described in Example 2. The results of these dissolution tests are provided in Table 3, below.

TABLE 3

| Control Dosage Form | Time (hr) | Azithromycin Released (mg) | Azithromycin Released (%) |
|---|---|---|---|
| 8 tablets | 0 | 0 | 0 |
| No TSP | 0.08 | 1100 | 55 |
| | 0.25 | 1480 | 74 |
| | 0.5 | 1600 | 80 |
| | 1 | 1700 | 85 |
| | 2 | 1720 | 86 |
| | 3 | 1700 | 85 |
| 8 tablets | 0 | 0 | 0 |
| 176 mg TSP | 0.08 | 1040 | 52 |
| | 0.25 | 1380 | 69 |
| | 0.5 | 1500 | 75 |
| | 1 | 1580 | 79 |
| | 2 | 1600 | 80 |
| | 3 | 1620 | 81 |

These results confirm that, when combined with an alkalizing agent, the release rate from an immediate release azithromycin dosage form is slowed.

EXAMPLE 5

Comparison of In Vitro Release Rates in Dosage Forms Having Different Azithromycin Multiparticulates The in vitro release rates of azithromycin, in 0.1 M $Na_2HPO_4$, were determined for various azithromycin sustained release dosage forms, which each contained 2 gA of different azithromycin multiparticulates and the same amount of a common alkalizing agent. The sustained release dosage forms were prepared as described in Step A, below, while the in vitro release rate study, and its results, are described in the following Step B.

Step A—Preparation of Azithromycin Sustained Release Dosage Forms

Six azithromycin sustained release dosage forms, specifically SR9, SR10, SR11, SR12, SR13 and SR14 were prepared by mixing azithromycin multiparticulates, respectively, MP2, MP3, MP4, MP5, MP6 or MP7, each, with the same blend of two alkalizing agents (i.e., 352 mg TSP and 250 mg magnesium hydroxide) and excipients (i.e., 19.36 g sucrose, 67 mg hydroxypropyl cellulose, 67 mg xanthan gum, 110 mg colloidal silicon dioxide, 400 mg titanium dioxide, 140 mg cherry flavoring and 230 mg banana flavoring).

Azithromycin Multiparticulates

Azithromycin multiparticulates "MP2", which comprised 50 wt % azithromycin dihydrate, 47 wt % Compritol®, and 3 wt % "Lutrol®", were made in the same manner as the MP1 multiparticulates in Example 2, with the exception that the blend was then fed through a B&P 19-mm twin-screw extruder, at a rate of 131 g/min, to form the molten mixture. Water was concurrently added to the extruder at a rate that provided a water content in the molten mixture of 2 wt % and the multiparticulates were post-treated for 21 days to form azithromycin multiparticulates with a mean diameter of about 188 microns.

Azithromycin multiparticulates "MP3", which comprised 50 wt % azithromycin dihydrate, 47 wt % Compritol®, and 3 wt % "Lutrol®", were made in the same manner as the MP2 multiparticulates in this Example, with the exception that the disk was rotating at 4800 rpm, to form azithromycin multiparticulates with a mean diameter of about 204 microns.

Azithromycin multiparticulates "MP4", which comprised 50 wt % azithromycin dihydrate, 47 wt % Compritol®, and 3 wt % "Lutrol®", were made in the same manner as the MP2 multiparticulates in this Example, with the exception that the disk was rotating at 4100 rpm, to form azithromycin multiparticulates with a mean diameter of about 227 microns.

Azithromycin multiparticulates "MP5" were made which comprised 50 wt % azithromycin multiparticulates, 48 wt % Compritol®, and 2 wt % Lutrol® in the same manner as MP1 in Example 1, with the exception that the blend was then fed through a Liestritz 27 mm twin-screw extruder, at a rate of 140 g/min, to form the molten mixture.

Azithromycin multiparticulates "MP6" were made comprising 50 wt % azithromycin dihydrate, 47 wt % Compritol®, and 3 wt % Lutrol® F127 using the following procedure. First, 15 kg azithromycin dihydrate, 14.1 kg of the Compritol® and 0.9 kg of the Lutrol® were weighed and passed through a Quadro 194S Comil mill in that order. The mill speed was set at 600 rpm. The mill was equipped with a No. 2C-075-H050/60 screen (special round), a No. 2C-1607-049 flat-blade impeller, and a 0.225-inch spacer between the impeller and screen. The de-lumped mixture was blended using a Servo-Lift 100-L stainless-steel bin blender rotating at 20 rpm, for a total of 500 rotations, forming a preblend feed.

The preblend feed was delivered to a Leistritz 50 mm twin-screw extruder (Model ZSE 50, American Leistritz Extruder Corporation, Somerville, N.J.) at a rate of 25 kg/hr. The extruder was operated in co-rotating mode at about 300 rpm, and interfaced with a melt/spray-congeal unit. The extruder had nine segmented barrel zones and an overall extruder length of 36 screw diameters (1.8 m). Water was injected into barrel number 4 at a rate of 8.3 g/min (2 wt %). The extruder's rate of extrusion was adjusted so as to produce a molten feed suspension of the azithromycin dihydrate in the Compritol®/Pluronic® at a temperature of about 90° C.

The molten feed suspension was delivered to a spinning-disk atomizer rotating at 7600 rpm, the surface of which was maintained at 90° C. The maximum total time the azithromycin dihydrate was exposed to the molten suspension was less than about 10 minutes. The particles formed by the spinning-disk atomizer were cooled and congealed in the presence of cooling air circulated through the product collection chamber. The mean particle size was determined to be 188 $\mu$m using a Horiba LA-910 particle size analyzer. Samples of the multiparticulates were also evaluated by PXRD, which showed that about 99% of the azithromycin in the multiparticulates was in the crystalline dihydrate form.

The so-formed multiparticulates were post-treated by placing samples in sealed barrels which were then placed in a controlled atmosphere chamber at 40° C. for 3 weeks.

Azithromycin multiparticulates "MP7", which comprised 50 wt % azithromycin dihydrate, 47 wt % Compritol®, and 3 wt % Lutrol® F127, were made as follows.

Azithromycin dihydrate (140 kg) was weighed and passed through a Quadro Comil 196S with a mill speed of 900 rpm. The mill was equipped with a No. 2C-075-H050/60 screen (special round, 0.075"), a No. 2F-1607-254 impeller, and a 0.225 inch spacer between the impeller and screen. Next, 8.4 kg of the Lutrol® and then 131.6 kg of the Compritol® were weighed and passed through a Quadro 194S Comil mill. The mill speed was set at 650 rpm. The mill was equipped with a No. 2C-075-R03751 screen (0.075"), a No. 2C-1601-001 impeller, and a 0.225-inch spacer between the impeller and screen. The milled mixture was blended using a Gallay 38 cubic foot stainless-steel bin blender rotating at 10 rpm for 40 minutes, for a total of 400 rotations, forming a preblend feed The preblend feed was delivered to a Leistritz 50 mm twin-screw extruder at a rate of about 20 kg/hr. The extruder was operated in co-rotating mode at about 100 rpm, and interfaced with a melt/spray-congeal unit. The extruder had five segmented barrel zones and an overall extruder length of 20 screw diameters (1.0 m). Water was injected into barrel number 2 at a rate of 6.7 g/min (2 wt %). The extruder's rate of extrusion was adjusted so as to produce a molten feed suspension of the azithromycin dihydrate in the Compritol®/Lutrol® at a temperature of about 90° C.

The feed suspension was delivered to a 10.1 cm diameter spinning-disk atomizer, described above in Example 2 which was rotating at 6400 rpm and maintaining a disk surface temperature of 90° C. The maximum total time the azithromycin was exposed to the molten suspension was less than 10 minutes. The particles formed by the spinning-disk atomizer were cooled and congealed in the presence of cooling air circulated through the product collection chamber. The mean particle size was determined to be about 200 μm using a Malvern particle size analyzer.

The so-formed multiparticulates were post-treated by placing a sample in a sealed barrel that was then placed in a controlled atmosphere chamber at 40° C. for 10 days. Samples of the post-treated multiparticulates were evaluated by PXRD, which showed that about 99% of the azithromycin in the multiparticulates was in the crystalline dihydrate form.

Step B—In Vitro Azithromycin Release Rate Study

The in vitro rates of release of azithromycin, for the sustained release dosage forms (2 gA each) SR9, SR10, SR11, SR12, SR13 and SR14 were determined by the following dissolution test method.

Water (60 mL) was added to the bottle containing the dosage form. The bottle was capped and then inverted several times to mix the suspension. Each sustained release dosage formulation, in suspension form, was tested by adding it to the dissolution buffer in a standard USP rotating paddle apparatus as disclosed in United States Pharmacopeia (USP 26), Dissolution Test, Chapter 711, Apparatus 2. Paddles were rotated at 50 rpm and the dissolution test was conducted in 840 mL of 0.1 M sodium phosphate buffer, pH 6.0 (±0.05) at 37±0.5° C. At indicated times following test initiation (i.e. insertion of the dosage form into the apparatus), filtered aliquots (typically 10 mL) from the test medium were analyzed for azithromycin by reverse-phase high performance liquid chromatography (HPLC) and UV detection as follows. An aliquot of test solution was filtered to remove particulates. A fixed volume of 10 μL was injected onto a column (15 cm length×3.9 mm ID) kept at 35±3° C. The mobile phase consisted of volume ratios of 45% acetonitrile, 30% methanol, and 25% buffer. The buffer consisted of 25 mM $KH_2PO_4$, pH 6.5. The flow rate was set at 1 mL/min. In the dissolution test media, actual quantification of azithromycin was determined by comparison of sample chromatogram peak area against an azithromycin standard chromatogram peak area.

TABLE 4

| Formulation | Time (hr) | Azithromycin Released (mgA) | Azithromycin Released (%) |
|---|---|---|---|
| SR9 (MP2) | 0.25 | 560 | 28 |
| | 0.5 | 920 | 46 |
| | 1 | 1400 | 70 |
| | 2 | 1800 | 90 |
| | 3 | 1900 | 95 |
| SR10 (MP3) | 0.25 | 520 | 26 |
| | 0.5 | 860 | 43 |
| | 1 | 1320 | 66 |
| | 2 | 1740 | 87 |
| | 3 | 1860 | 93 |
| SR11 (MP4) | 0.25 | 500 | 25 |
| | 0.5 | 800 | 40 |
| | 1 | 1240 | 62 |
| | 2 | 1680 | 84 |
| | 3 | 1840 | 92 |
| SR12 (MP5) | 0.25 | 460 | 23 |
| | 0.5 | 760 | 38 |
| | 1 | 1180 | 59 |
| | 2 | 1460 | 73 |
| | 3 | 1640 | 82 |
| SR13 (MP6) | 0.25 | 600 | 30 |
| | 0.5 | 1000 | 50 |
| | 1 | 1540 | 77 |
| | 2 | 1920 | 96 |
| | 3 | 1980 | 99 |

TABLE 4-continued

| Formulation | Time (hr) | Azithromycin Released (mgA) | Azithromycin Released (%) |
|---|---|---|---|
| SR14 (MP7) | 0.25 | 730 | 37 |
| | 0.5 | 1200 | 60 |
| | 1 | 1700 | 85 |
| | 2 | 1880 | 94 |
| | 3 | 1920 | 96 |

The results of these dissolution tests, provided above in Table 4, show that these various formulations, of multiparticulates and alkalizing agent, meet the release rate criterion for the pH 6.0 buffer in vitro test of (i) from 15 to 55 wt % of said azithromycin in said dosage form at 0.25 hour; (ii) from 30 to 75 wt % of said azithromycin in said dosage form at 0.5 hour; and (iii) greater than 50 wt % of said azithromycin in said dosage form at 1 hour after administration to the buffer test medium.

EXAMPLE 6

In Vivo Comparison of Azithromycin Sustained Release Dosage Forms and an Immediate Release Azithromycin Dosage Form Two clinical studies were conducted to respectively evaluate the pharmacokinetics and gastrointestinal toleration of three azithromycin sustained release dosage forms, of the present invention, each of which contained 352 mg anhydrous TSP as an alkalizing agent and optionally contained 250 mg magnesium hydroxide, as compared to an azithromycin immediate release dosage form which contained half as much TSP (176 mg) and no magnesium hydroxide. The sustained release dosage forms were prepared as described in Step A, below, while the pharmacokinetics and side effects clinical studies, and their results, are described, respectively, in the following Steps B and C.

Step A—Preparation of Azithromycin Sustained Release Dosage Forms

These sustained release dosage forms were prepared as follows. Two different azithromycin sustained release dosage forms (hereinafter "SR15" and "SR16") were prepared by mixing 4.2 g (2 gA) of azithromycin multiparticulates, prepared as described below, with different excipients. The SR15 dosage form comprised a mixture of the azithromycin multiparticulates and the excipient blend, described below. The SR16 dosage form comprised a mixture of the azithromycin multiparticulates, the same excipient blend, and magnesium hydroxide. To prepare SR16, magnesium hydroxide was added to the bottle containing SR15. The contents were mixed by swirling the bottle.

SR12 was prepared as described in Example 5.

Azithromycin Multiparticulates

Azithromycin multiparticulates "MP8", which comprised 50 wt % azithromycin dihydrate, 47 wt % Compritol®, and 3 wt % Lutrol®, were made in the same manner as the MP1 multiparticulates in Example 2, with the exception that the blend was then fed through a Leistritz 27 mm twin-screw extruder (Model ZSE 27, American Leistritz Extruder Corporation, Somerville, N.J.), at a rate of 140 g/min, to form the molten mixture.

Alkalizing Agents and Excipients

An excipient blend, for use in combination with the azithromycin multiparticulates, was prepared. The excipient blend consisted of a mixture of 352 mg anhydrous TSP as an alkalizing agent, 19.36 g sucrose (NF), 67 mg hydroxypropyl cellulose (NF), 67 mg xanthan gum (NF), 200 mg colloidal silicon dioxide (NF), 400 mg titanium dioxide (USP), 140 mg cherry flavoring and 230 mg banana flavoring.

Separate bottles, containing 250 mg of the optional alkalizing agent magnesium hydroxide (USP), were also prepared.

Step B—Pharmacokinetics Clinical Study

The in vivo pharmacokinetics of the "SR15" and "SR16" azithromycin multiparticulate dosage forms were evaluated in 32 fasting, healthy human subjects in a randomized, open-label, parallel group, two way cross-over study. On Day 1, eight subjects received the SR15 azithromycin multiparticulate dosage form and eight subjects received the SR16 azithromycin multiparticulate dosage form. As controls, two groups (A and B) of eight subjects each received two single dose packets of azithromycin dihydrate for oral suspension (Zithromax®, Pfizer Inc., New York, N.Y.) wherein each dose contains 1048 mg azithromycin dihydrate, which is equivalent to 1000 mgA azithromycin, 88 mg TSP and the inactive ingredients previously noted.

Specifically, 2 gA of either of the azithromycin formulations (SR15 without magnesium hydroxide or SR16 with magnesium hydroxide) or commercially available azithromycin sachets, were dosed based upon the computer-generated randomization for each of the two treatment groups.

To dose the SR15 and SR16 formulations, 60 mL of water was added to the bottle containing SR15 and was shaken for 30 seconds. The entire contents of the bottle were administered directly into the subject's mouth. An additional 60 mL of water was added to rinse the bottle and the rinse was administered to the subject's mouth. An additional 120 mL of water was administered using a dosing cup.

To dose azithromycin commercial two 1 g sachets, the contents of 1 g Zithromax® single dose packet were emptied into a cup containing 60 mL of water. The mixture was stirred and was administered to the subject's mouth. An additional 60 mL of water was used to rinse the cup and the rinse was administered. This procedure was repeated for the second Zithromax® Single Dose Packet.

All subjects were orally dosed after an overnight fast. All subjects were then required to refrain from lying down, eating and drinking beverages other than water during the first 4 hours after dosing.

Blood samples (5 mL each) were withdrawn from the subjects' veins prior to dosing, and at 0.5, 1, 2, 3, 4, 6, 8, 12, 16, 24, 36, 48, 72 and 96 hr post-dosing. Serum azithromycin concentrations were determined using the high performance liquid chromatography assay described in Shepard et al., J Chromatography. 565:321–337 (1991). Total systemic exposure to azithromycin was determined by measuring the area under the curve (AUC) for each subject in the group and then by calculating a mean AUC for the group. Cmax is the highest serum azithromycin concentration achieved in a subject. Tmax is the time at which Cmax is achieved. % CV is the coefficient of variance and SD is the standard deviation.

On Day 15, the procedure was repeated except that the two 8-subject groups, who received control dosage forms on Day 1, were then dosed with azithromycin multiparticulate dosage forms SR15 or SR16. Likewise, the two 8-subject groups, who previously received the azithromycin multiparticulate dosage forms on Day 1, were then dosed with the control dosage forms.

An in vivo pharmacokinetics of the SR12 azithromycin multiparticulate dosage form was also evaluated in sixteen fasting, healthy human subjects in a randomized, two-way cross-over study. The control was two single dose packets of azithromycin dihydrate for oral suspension (Zithromax®, Pfizer Inc., New York, N.Y.) wherein each dose contains 1048 mg azithromycin dihydrate, which is equivalent to 1000 mgA azithromycin, 88 mg TSP and the inactive ingredients previously noted.

The results of this study are provided in Table 5.

TABLE 5

| Formulation | $C_{max}$ ($\mu$g/mL) Geometric Mean | % CV | $T_{max}$ (hr) Arithmetic Mean | SD | AUC ($\mu$g · hr/mL) 0–Tlast (96 hrs) Geometric Mean | % CV |
|---|---|---|---|---|---|---|
| SR15 | 0.92 | 36 | 2.94 | 1.7 | 13.81 | 35 |
| SR16 | 0.82 | 26 | 4.13 | 1.6 | 15.75 | 40 |
| Control for SR15 | 2.09 | 36 | 1.13 | 0.3 | 18.98 | 22 |
| Control for SR16 | 1.90 | 49 | 1.56 | 0.7 | 19.03 | 24 |
| SR12 | 0.86 | 26 | 4.88 | 1.86 | 13.6 | 25 |
| Control for SR12 | 2.10 | 42 | 1.25 | 0.58 | 15.3 | 24 |

Based upon the results in Table 5, the bioavailabilities for SR15, SR16 and SR12 were 73%, 83% and 89%, respectively, relative to the immediate release control dosage form. The data also showed that the ratios of the maximum serum concentration of azithromycin provided by the multiparticulate dosage forms SR15, SR16 and SR12 to the maximum serum concentration of azithromycin provided by the Control Dosage Form were 0.44, 0.43 and 0.41, respectively. In addition, the time to achieve the maximum serum concentration was longer for the azithromycin multiparticulate dosage forms than for the immediate release control dosage forms.

Step C—Gastrointestinal Toleration Clinical Study

The in vivo toleration of the SR15 and SR16 azithromycin multiparticulate dosage forms were evaluated through a randomized, parallel group study. Specifically, 106 healthy human subjects were orally administered the SR15 sustained release azithromycin multiparticulate formulation, 106 healthy human subjects were orally administered the SR16 sustained release azithromycin multiparticulate formulation, and 108 healthy human subjects were each administered two single dose 1 gA packets of azithromycin dihydrate for oral suspension by the following procedure. The entire contents of one packet were mixed with approximately 60 mL of water in a cup and then drunk immediately. An additional 60 mL of water was added to the cup, mixed and then drunk to assure complete consumption of the dosage. These steps were then repeated for the second packet.

GI adverse events, such as diarrhea, nausea, and vomiting, were monitored for 48 hours following administration of each dosage form. Subjects were verbally queried at least at the following approximate times: 1, 2, 4, 6, 8, 12 and 24 hours after dosing by asking non-leading questions.

The incidence of gastrointestinal adverse events, experienced by the subjects tested, are provided in Table 6.

A similar in vivo toleration study was performed on the formulation SR12 using a population of 16 healthy human subjects. The control used for this study was two single dose 1 gA packets of azithromycin dihydrate for oral suspension. The results of this study are also provided in Table 6.

TABLE 6

| Formulation | Percentage of Subjects with GI Adverse Events | | |
|---|---|---|---|
| | Diarrhea | Nausea | Vomiting |
| SR15 | 17.9 | 17.0 | 2.8 |
| SR16 | 23.6 | 17.0 | 3.8 |
| Control | 27.8 | 54.6 | 25.9 |
| SR12 | 18.8 | 18.8 | 0 |
| Control for SR12 | 18.8 | 50 | 6 |

The results in Table 5 and 6 show that both azithromycin multiparticulate dosage forms, with or without magnesium hydroxide, wherein the multiparticulates included 2–3 wt % Lutrol®, provided lower immediate concentrations of azithromycin released from the forms, as compared to the immediate release Control Dosage Form, and substantially improved gastrointestinal toleration relative to the immediate release Control Dosage Form while concurrently maintaining a bioavailability substantially equivalent to the immediate release control. Further, SR15 provided a relative degree of improvement, as compared to the control, of 1.6 for diarrhea, 3.2 for nausea, and 9.3 for vomiting while SR16 provided a relative degree of improvement of 1.2 for diarrhea, 3.2 for nausea, and 6.8 for vomiting. Likewise, SR12 provided no improvement in diarrhea over the control, a relative degree of improvement of 50 and no vomiting events as compared to the 6 events that occurred with the control. Note that the results for SR12 cannot be accurately compared to those for SR15 and SR16 due to the small population size of the SR12 study.

EXAMPLE 7

In Vivo Comparison of Azithromycin Multiparticulate Forms and an Immediate Release Azithromycin Dosage Form A clinical study was conducted to evaluate the pharmacokinetics and gastrointestinal toleration of two azithromycin multiparticulate dosage forms which contained 2 gA or 3 gA of azithromycin, respectively, and each of which contained 352 mg anhydrous TSP as an alkalizing agent, as compared to an azithromycin immediate release dosage form which contained half as much TSP (176 mg) and no magnesium hydroxide. The sustained release dosage form was prepared as described in the following Step A, an in vitro release rate study of the 2 gA dosage form was performed as described in Step B, while the pharmacokinetics and side effects clinical studies, and their results, are described, respectively, in the following Steps C and D.

Step A—Preparation of Azithromycin Multiparticulate Dosage Forms

Azithromycin multiparticulate dosage forms (hereinafter "SR17" and SR"18") were prepared by mixing 4.2 g (2 gA) or 6.3 g (3 gA), respectively, of azithromycin multiparticulates MP9 which prepared as described below, with excipients. The SR17 dosage form comprised a mixture of the azithromycin multiparticulates (MP9) and the excipient blend, described below.

Azithromycin Multiparticulates

Azithromycin multiparticulates "MP9", which comprised 50 wt % azithromycin dihydrate, 46 wt % Compritol®, and 4 wt % Lutrol®, were made in the same manner as the MP9 multiparticulates in Example 2, with the exception that the blend was fed through a Liestritz 27 mm twin-screw extruder, at a rate of 140 g/min, to form the molten mixture. The spinning disk atomizer was rotated at 5500 rpm to form the multiparticulates. The resulting multiparticulates were exposed to 40° C. and 75% relative humidity in an environmental chamber for 5 days.

Alkalizing Agents and Excipients

An excipient blend, for use in combination with the azithromycin multiparticulates, was prepared. The excipient blend consisted of a mixture of 352 mg anhydrous TSP as an alkalizing agent, 38.7 g sucrose (NF), 67 mg hydroxypropyl cellulose (NF), 67 mg xanthan gum (NF), 200 mg colloidal silicon dioxide (NF), 400 mg titanium dioxide (USP), 140 mg cherry flavoring, 330 mg vanilla flavoring and 230 mg banana flavoring.

Step B—In Vitro Azithromycin Release Rate Study

An in vitro release rate study of multiparticulate dosage form SR 17 was performed as described in Example 5.

TABLE 7

| Formulation | Time (hr) | Azithromycin Released (mgA) | Azithromycin Released (%) |
|---|---|---|---|
| SR17 (MP9) | 0.25 | 1080 | 54 |
| | 0.5 | 1540 | 77 |
| | 1 | 1880 | 94 |
| | 2 | 1920 | 96 |
| | 3 | 1920 | 96 |

Step C—Pharmacokinetics Clinical Study

The in vivo pharmacokinetics of the SR17 and SR18 azithromycin multiparticulate dosage forms were evaluated in 300 fasting, healthy human subjects (100 subjects per treatment group) in a randomized, parallel group study. Subjects are randomly assigned to one of the following 3 treatment groups: SR17 (2 gA), SR18 (3 gA) and 8×250 mgA Zithromax® tablets (control) which, in combination, contain 2 gA azithromycin, 1.1 g dibasic sodium phosphate and other inactive ingredients.

For all doses, a total volume of 240 mL of water was consumed. To dose the SR17 and SR18 formulations, SR17 or SR18 was added to the bottle containing the excipient blend. Water (60 mL) was added to this bottle containing SR17 or SR18 and the excipient blend. The bottle was shaken for 30 seconds to mix the suspension. The entire contents of the bottle were administered directly into the subject's mouth. An additional 60 mL of water was added to rinse the bottle and the rinse was administered to the subject's mouth. An additional 120 mL of water was administered using a dosing cup.

To dose the eight commercial Zithromax® 250 mg tablets, the subjects were given 240 mL of water to orally administer eight tablets one by one.

All subjects were orally dosed after an overnight fast. All subjects were then required to refrain from lying down, eating and drinking beverages other than water during the first 4 hours after dosing.

Sufficient blood was withdrawn from each subject to provide a minimum of 3 ml serum for azithromycin pharmacokinetics. The blood was collected in tubes having no preservative or anticoagulant or serum separator at the following times: 0 (Just prior to dosing), 2 and 3 hours (around projected Tmax) after drug administration. Serum azithromycin concentrations were determined using the high performance liquid chromatography assay described in Shepard et al., J Chromatography. 565:321–337 (1991).

The results of this study are provided in Table 8.

TABLE 8

| Formulation | Serum azithromycin concentration (μg/mL) at 2 hour post dosing | Serum azithromycin concentration (μg/mL) at 3 hour post dosing |
|---|---|---|
| SR17 | 1.04 | 0.933 |
|  | % CV 36 | % CV 34 |
| SR18 | 1.57 | 1.26 |
|  | % CV 47 | % CV 25 |
| Tablets (8 × 250 mg) | 1.08 | 0.962 |
|  | % CV 37 | % CV 32 |

Based upon the results in Table 8, the serum azithromycin concentration for SR17 and SR18 at 2 hours and 3 hours after dosing were no less than the serum concentrations for 8 Zithromax® tablets. The data indicated that there was no delay of drug release from SR17 or SR18 given the amount of alkalizing agent administered.

Step D—Gastrointestinal Toleration Clinical Study

The toleration of the SR17 and SR18 azithromycin multiparticulate dosage forms tested in Step B was evaluated. On day 1 subjects were verbally queried for adverse events at least at the following approximate times: 0, 2, 4, 8, 12 and 24 hours. The incidence of gastrointestinal adverse events, experienced by the subjects tested, are provided in Table 9.

TABLE 9

| Formulation | Number of Subjects with GI Adverse Events |  |  |
|---|---|---|---|
|  | Diarrhea | Nausea | Vomiting |
| SR17 | 44 | 28 | 6 |
| SR18 | 59 | 51 | 9 |
| Control (8 × 250 mg tablets) | 39 | 30 | 7 |

The results in Tables 7 and 8 show that the 2 gA or 3 gA azithromycin multiparticulate dosage forms tested, wherein the multiparticulates included 4 wt % Lutrol® and the excipient blend having TSP in the amount of 352 mg, provided no advantage in lowering serum concentration or improving GI toleration as compared to the immediate release tablet dosage form.

Thus, as exhibited by the results in Tables 8 and 9, an effective amount of alkalizing agent was not used with these specific multiparticulates to provide the desired release and GI side effects profiles.

EXAMPLE 8

Method for Determining Alkalizing Agent to be Used with Immediate Release Azithromycin The effective amount of alkaline agent that would suppress the dissolution of azithromycin in the stomach and thereby result in an improvement in the toleration of the immediate release (IR) formulation was calculated as follows. The IR formulation, without an alkalizing agent, releases about 92% of the drug in 30 minutes at pH 6.0 as described in Example 5, i.e., 3.07% per minute at pH 6.0. To improve the toleration, the azithromycin dissolution rate must be reduced, preferably to a rate that will release only about 1.5 gA, or less, in the first 30 minutes or no greater than 2.5% per minute. It was assumed that the rate of drug dissolution from an IR formulation is directly proportional to the solubility of azithromycin, which is dependent on the pH as shown in Table 10.

TABLE 10

| pH | Azithromycin Solubility (mg/mL) |
|---|---|
| 2.88 | 440 |
| 4.09 | 430 |
| 6.15 | 380 |
| 6.42 | 310 |
| 6.61 | 250 |
| 6.65 | 140 |
| 6.75 | 120 |
| 6.87 | 36 |
| 7.41 | 5 |
| 8.02 | 0.5 |
| 8.85 | 0.02 |
| 10.34 | 0.005 |

Because it was assumed that the azithromycin release rate is directly proportional to its solubility, the azithromycin solubility at pH 6.0, at a rate of 3.07%, is 390 mg/mL which was obtained by interpolation from Table 10. The corresponding solubility that would give improved toleration is calculated as:

$$\text{Solubility}^T = (390 \text{ mg/mL})(2.5\%)/(3.07\%)$$

Solubility$^T$ is defined as the solubility at which the dissolution of azithromycin does not result in excessive GI adverse effects. Solubility$^T$ from the equation was found to be 318 mg/mL. Again, by interpolation from Table 10 the pH corresponding to solubility$^T$ is 6.4.

Preferably, the amount of alkalizing agent formulated with IR azithromycin, or which is co-dosed with IR azithromycin, is that which, when dosed, will raise the pH in the stomach to 6.63 for at least 30 minutes. To calculate this amount, it is assumed that the basal amount of acid in the stomach is around 0.96 mmol H+ and that the average acid secretion rate is about 3 mmol per hour.

To calculate the amount of alkalizing agent or alkalizing agents that should be included in the formulation, we need titration data for various alkalizing agents and combinations of alkalizing agents was performed. Thus, solutions of several alkalizing agents and combinations of alkalizing agents were made and titrated with 0.1 N HCl and the resultant pH values were measured. From these data, one we can calculate a pH versus time profile as described in Step A of Example 1 assuming that the basal amount of acid in the stomach is around 0.96 mmol H+ and that the average acid secretion rate is about 3 mmol per hour. These data are presented in FIGS. 2 and 3.

Figure 3:
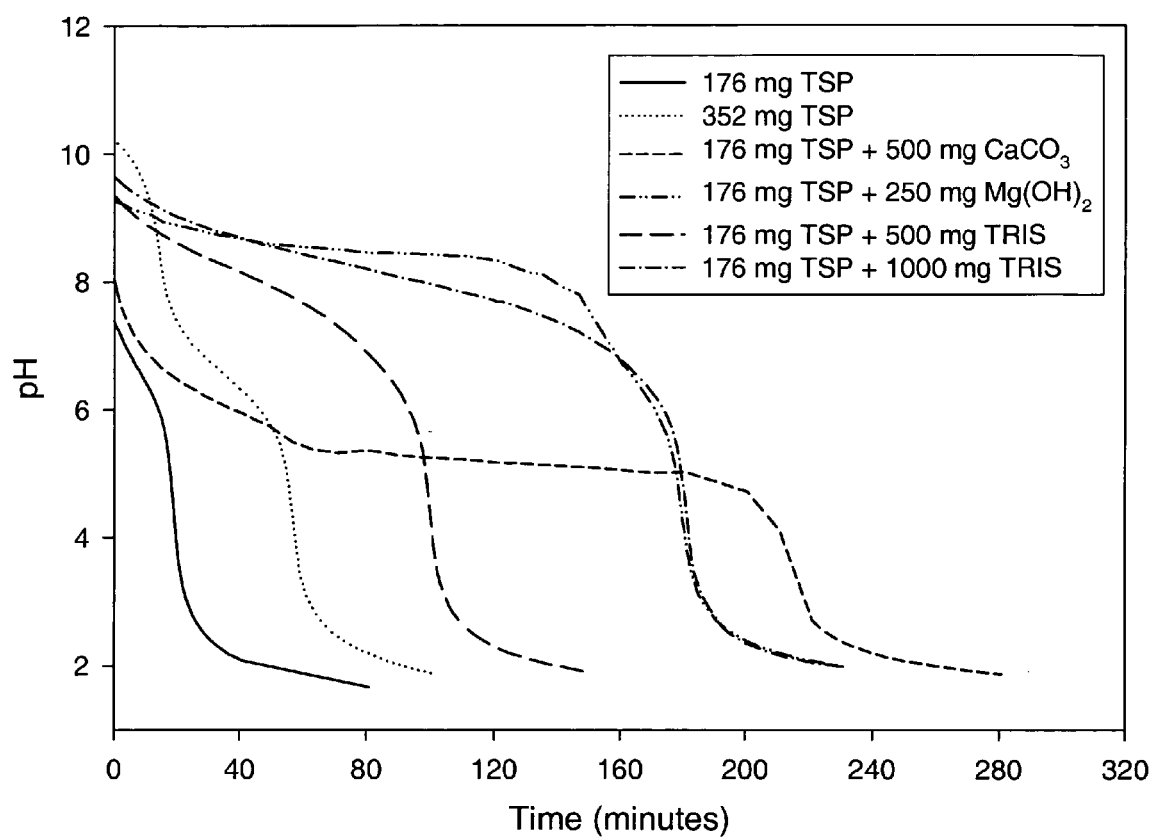
FIG. 3, which is further discussed in Example 8, shows the calculated pH of different alkalizing agents when titrated with 0.1N HCl over time.

From FIG. 3, it is seen that Formulations containing 176 mg TSP or 176 mg TSP plus 500 mg CaCO$_3$ are not expected to increase gastric pH to 6.8 for a period of 30 to 40 minutes while formulations containing (76 mg TSP and 500 mg TRIS, 176 mg TSP plus 1000 mg TRIS, or 176 mg TSP plus 250 mg Mg(OH)$_2$ are expected to provide the increased pH for at least that long. Formulation with 352 mg TSP appears to provide pH 6.48 for just a bit over 30 minutes and can therefore be considered as containing the minimum amount of alkalizing agent needed for reducing GI side effects following administration of a high dose IR formulation of azithromycin. Considering inter-individual differences in the gastric acid secretion rates and considering robust performance of a dosage form, a quantity of alkalizing agent higher than the minimum is preferred.

By a similar analysis of the data in FIG. 2, 352 mg TSP and 352 mg TSP+500 mg calcium carbonate are predicted to barely provide adequate increased gastric pH for the desired duration while the remaining combinations tested are predicted to provide adequate increase in gastric pH for the desired time period. It should be noted that the above general procedure to determine the effective amount of alkalizing agent is dependent upon the assumptions made about the basal acid conditions in the stomach and the acid secretion rate. The values selected represent averages for generally healthy individuals and there can be significant inter-individual and within-individual variability. The effective amount of alkalizing agent under a different set of assumptions can be calculated by following the procedure outlined above.

We claim:

1. An oral dosage form comprising:
   (a) an effective amount of an alkalizing agent; and
   (b) multiparticulates wherein said multiparticulates comprise (i) about 20% to about 75% azithromycin, and (ii) about 25% to about 80% of a glyceride which comprises glyceryl monobehenate, glyceryl dibehenate, glyceryl tribehenate or a mixture thereof; and (iii) a poloxamer.

2. An oral dosage form of claim 1 wherein the poloxamer comprises poloxamer 407.

3. An oral dosage form of claim 1 wherein the alkalizing agent comprises a bicarbonate, a phosphate, a metal hydroxide, a metal oxide or a combination thereof.

4. An oral dosage form of claim 3 wherein the alkalizing agent comprises tribasic sodium phosphate and magnesium hydroxide.

5. An oral dosage form of claim 3 further comprising about 250 mgA to about 7 gA of azithromycin.

6. An oral dosage form of claim 5 further comprising about 1.5 gA to about 4 gA of azithromycin.

7. An oral dosage form of claim 5 further comprising 1.8 to 2.2 gA of azithromycin.

8. An azithromycin oral dosage form, comprising:
   (a) at least about 200 mg of tribasic sodium phosphate; and
   (b) multiparticulates, wherein said multiparticulates comprise (i) azithromycin, (ii) a mixture of glyceryl monobehenate, glyceryl dibehenate and glyceryl tribehenate, and (iii) poloxamer 407, and wherein said dosage form contains about 1.5 gA to about 4 gA of azithromycin.

9. An oral dosage form of claim 8, further comprising at least about 100 mg of magnesium oxide.

10. An oral dosage form of claim 8, comprising:
    (a) 300 mg to 400 mg of tribasic sodium phosphate;
    (b) 200 mg to 300 mg of magnesium hydroxide; and
    (c) multiparticulates, wherein said multiparticulates comprise (i) azithromycin, (ii) a mixture of glyceryl monobehenate, glyceryl dibehenate and glyceryl tribehenate, and (iii) poloxamer 407,
    and wherein said dosage form contains about 1.5 gA to about 4 gA of azithromycin.

11. An oral dosage form of claim 8 further comprising 1.8 to 2.2 gA of azithromycin.

12. An oral dosage form of claim 11 wherein said azithromycin is azithromycin dihydrate.

13. An oral dosage form of claim 1 wherein said azithromycin is azithromycin dihydrate.

14. An oral dosage form of claim 3 wherein said azithromycin is at least 70 wt % crystalline.

15. An oral dosage form of claim 3 wherein said oral dosage form is a powder for oral suspension, a unit dose packet, an oral suspension, a tablet or a capsule.

16. A method for reducing the frequency of gastrointestinal side effects, associated with administering azithromycin to a mammal, comprising contiguously administering oral dosage form of claim 1 to said mammal wherein the frequency of gastrointestinal side effects is reduced as compared to the frequency experienced when administering an equal dose of azithromycin without said alkalizing agent.

17. A method of claim 16 wherein said mammal is a human.

18. A method of claim 17 further comprising administering between about 250 mgA and about 7 gA of azithromycin to said human.

19. A method of claim 18 wherein the azithromycin is administered in a single dose.

20. A method of claim 19 further comprising administering between about 1.5 and about 4 gA of azithromycin.

21. A method of claim 19 further comprising administering between about 1.5 and about 3 gA of azithromycin.

22. A method of claim 19 further comprising administering between 1.8 and 2.2 gA of azithromycin to said human in a single dose.

23. A method of claim 17 further comprising administering between 30 mgA/kg and 90 mgA/kg of azithromycin to a human, wherein said human is a child weighing 30 kg or less.

24. A method of claim 23 wherein the azithromycin is administered in a single dose.

25. A method of claim 24 further comprising administering between 45 mgA/kg and 75 mgA/kg of azithromycin to a child weighing 30 kg or less.

26. A method of claim 24 further comprising administering about 60 mgA/kg of azithromycin to a child weighing 30 kg or less.

27. A method of claim 16 wherein the alkalizing agent further comprises a bicarbonate, a phosphate, a metal hydroxide, a metal oxide, or a combination thereof.

28. A method of claim 27 wherein the alkalizing agent comprises tribasic sodium phosphate and magnesium hydroxide.

29. A method of claim 27 wherein said azithromycin comprises an immediate release form of azithromycin.

30. A method of claim 27 wherein said azithromycin comprises a sustained release form of azithromycin.

31. A method of claim 27 wherein said azithromycin comprises azithromycin multiparticulates.

32. A method of claim 31 wherein said azithromycin multiparticulates comprise:
    (a) azithromycin; and
    (b) a pharmaceutically acceptable carrier.

33. A method of treating a bacterial or protozoal infection in a mammal in need thereof comprising administering to said mammal a single dose of an oral dosage form of claim 1.

34. A method of claim 33 wherein said mammal is a human.

35. A method of claim 34 further comprising administering between about 250 mgA and about 7 gA of azithromycin to said human.

36. A method of claim 35 wherein the azithromycin is administered in a single dose.

37. A method of claim 36 further comprising administering between about 1.5 and about 4 gA of azithromycin to said human.

38. A method of claim 36 further comprising administering between about 1.5 and about 3 gA of azithromycin to said human.

39. A method of claim 36 further comprising administering 1.8 gA to 2.2 gA of azithromycin to said human.

40. A method of claim 34 further comprising administering between 30 mgA/kg and 90 mgA/kg of azithromycin to said human, wherein said human is a child weighing 30 kg or less.

41. A method of claim 34 wherein the azithromycin is administered in a single dose.

42. A method of claim 41 further comprising administering between 45 mgA/kg and 75 mgA/kg of azithromycin to a child weighing 30 kg or less.

43. A method of claim 41 further comprising administering 60 mgA/kg of azithromycin to a child weighing 30 kg or less.

44. A method of claim 33 wherein the alkalizing agent comprises a bicarbonate, a phosphate, a metal hydroxide, a metal oxide, or a combination thereof.

45. A method of claim 44 wherein the alkalizing agent comprises tribasic sodium phosphate.

46. A method of claim 45 wherein the alkalizing agent further comprises magnesium hydroxide.

47. A method of claim 44 wherein said azithromycin comprises an immediate release form of azithromycin.

48. A method of claim 44 wherein said azithromycin comprises a sustained release form of azithromycin.

* * * * *